(12) United States Patent
Takabayashi

(10) Patent No.: US 7,084,184 B2
(45) Date of Patent: Aug. 1, 2006

(54) ACTINIC RAY CURABLE COMPOSITION, ACTINIC RAY CURABLE INK, IMAGE FORMING METHOD, AND INK JET RECORDING APPARATUS

(75) Inventor: Toshiyuki Takabayashi, Hachioji (JP)

(73) Assignee: Konica Corporation, Tokyo (JP)

( * ) Notice: Subject to any disclaimer, the term of this patent is extended or adjusted under 35 U.S.C. 154(b) by 149 days.

(21) Appl. No.: 10/647,170

(22) Filed: Aug. 21, 2003

(65) Prior Publication Data

US 2004/0052967 A1 Mar. 18, 2004

(30) Foreign Application Priority Data

Aug. 30, 2002 (JP) .............................. 2002-252368
Aug. 30, 2002 (JP) .............................. 2002-252369

(51) Int. Cl.
*G03C 1/73* (2006.01)
*G03F 7/004* (2006.01)
*C09D 11/10* (2006.01)

(52) U.S. Cl. ............................ 522/81; 522/83; 522/75; 522/168; 427/466

(58) Field of Classification Search ................. 522/81, 522/83, 75, 168; 427/466
See application file for complete search history.

(56) References Cited

U.S. PATENT DOCUMENTS

| | | | | |
|---|---|---|---|---|
| 4,394,403 A | * | 7/1983 | Smith | .......................... 427/500 |
| 5,674,922 A | * | 10/1997 | Igarashi et al. | ............. 522/168 |
| 6,084,004 A | | 7/2000 | Weinmann et al. | |
| 6,284,898 B1 | * | 9/2001 | Moszner et al. | ............ 549/214 |
| 6,365,760 B1 | * | 4/2002 | Kuriyama et al. | .......... 549/510 |
| 6,495,636 B1 | * | 12/2002 | Sugiyama et al. | ....... 525/326.3 |
| 6,617,418 B1 | * | 9/2003 | Magnusson et al. | ........ 528/417 |
| 6,783,840 B1 | * | 8/2004 | Watanabe et al. | ........... 428/209 |
| 6,794,451 B1 | * | 9/2004 | Sasaki et al. | ............. 525/92 R |
| 6,805,439 B1 | * | 10/2004 | Maeda et al. | ................. 347/96 |
| 6,846,074 B1 | * | 1/2005 | Hirai | .......................... 347/102 |
| 6,959,986 B1 | * | 11/2005 | Ushirogouchi et al. | ..... 347/100 |
| 2004/0023157 A1 | * | 2/2004 | Feiring et al. | ........... 430/272.1 |
| 2004/0050292 A1 | * | 3/2004 | Nakajima et al. | ......... 106/31.27 |
| 2004/0052968 A1 | * | 3/2004 | Takabayashi | ............... 427/511 |
| 2004/0222960 A1 | * | 11/2004 | Suzuki et al. | ................. 345/98 |

FOREIGN PATENT DOCUMENTS

GB 2 310 211 A 8/1997

(Continued)

*Primary Examiner*—Susan Berman
(74) *Attorney, Agent, or Firm*—Frishauf, Holtz, Goodman & Chick, P.C.

(57) ABSTRACT

Disclosed are an actinic ray curable composition, an actinic ray curable ink, an image recording method, and an ink jet recording apparatus, the actinic ray curable composition containing a photo acid generator, and an oxetane compound I represented by the following formula 1,

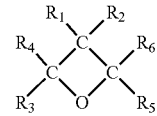

Formula 1 wherein $R_1$, $R_2$, $R_3$, $R_4$, $R_5$, and $R_6$ independently represent a hydrogen atom, a fluorine atom, an alkyl group having from 1 to 6 carbon atoms, a fluoroalkyl group having from 1 to 6 carbon atoms, an allyl group, an aryl group, a furyl group or a thienyl group, and wherein the longer C—O bond distance of the two C—O bond distances in formula 1 is from 0.1464 to 0.1500 nm.

8 Claims, 1 Drawing Sheet

| | FOREIGN PATENT DOCUMENTS | | | | |
|---|---|---|---|---|---|
| JP | 05-54667 | 3/1993 | JP | 2000-256571 A | 9/2000 |
| JP | 06-020204 A | 1/1994 | JP | 2001-181386 A | 7/2001 |
| JP | 08-143806 A | 6/1996 | JP | 2001-220526 | 8/2001 |
| JP | 2679586 | 8/1997 | JP | 2002-137375 | 5/2002 |
| JP | 2000-504778 A | 4/2000 | | | |

* cited by examiner

ACTINIC RAY CURABLE COMPOSITION, ACTINIC RAY CURABLE INK, IMAGE FORMING METHOD, AND INK JET RECORDING APPARATUS

FIELD OF THE INVENTION

The present invention relates to an actinic ray curable composition, an actinic ray curable ink, an image recording method, and an ink jet recording apparatus, which stably form an image with high resolution and excellent character quality, and exhibit no color contamination on various kinds of recording materials under various circumstances.

BACKGROUND OF THE INVENTION

In recent years, an ink jet recording method has found wide application in various kinds of graphic art fields such as photography, various kinds of printing, marking and specific printing such as a color filter because of being able to form images easily and inexpensively. Particularly, it has also become possible to obtain image quality comparable to silver salt photograph images by utilizing a recording apparatus which ejects and controls fine dots, ink in which a color reproduction range, durability and ejection suitability have been improved, and exclusive paper in which ink absorption, color forming property of colorants and surface gloss have been greatly improved. Image quality improvement of an ink jet recording method of today has been achieved only when a complete set of a recording apparatus, ink and exclusive paper is prepared.

However, an ink jet system which requires exclusive paper is problematic in respect to limitation of a recording medium and cost up of a recording medium. Therefore, many attempts have been made which record on a recording medium different from exclusive paper, employing an ink jet recording. Concretely, there are methods such as a phase-conversion ink jet method utilizing wax which is solid at room temperature, a solvent-type ink jet method utilizing an ink which is mainly comprised of a rapid-drying organic solvent and a UV ink jet method in which an ink is cross-linked by ultraviolet (UV) light after recording.

Among them, a UV ink jet method has been noted recently in respect to odor relatively lower than that of a solvent-type ink jet method, rapid drying property and capability of recording on a recording medium having no ink absorption. UV-curable ink jet inks are disclosed, for example, in Japanese Patent Publication No. 5-54667, JP-A (hereinafter, JP-A refers to Japanese Patent Publication Open to Public Inspection) No. 6-20204 and Japanese Translated PCT Patent Publication No. 2000-504778.

However, even when these inks are employed, the dot diameter of ink ejected onto recording material changes significantly depending on the kind of recording material or operating conditions, and it is therefore impossible to form an image with high resolution on various recording materials.

As UV-curable inks, there are a radical polymerization type UV-curable ink, which is comprised mainly of an acryl composition, and a cation polymerization type UV-curable ink.

The radical polymerization type UV-curable ink has problems in that the polymerization reaction is inhibited by oxygen on account of its polymerization mechanism, resulting in lowering of curability. In contrast, the cation polymerization type UV-curable ink is not influenced by oxygen, however, it has problem in that the polymerization reaction is susceptible to moisture in the molecular level on account of its polymerization mechanism.

SUMMARY OF THE INVENTION

The present invention has been made in view of the above. An object of the invention is to provide an actinic ray curable composition and an actinic ray curable ink, which provide an image with high resolution and excellent character quality, without causing color contamination under various recording circumstances, and an image recording method and an ink jet recording apparatus each employing the actinic ray curable ink.

DESCRIPTION OF THE INVENTION

Figure 1:
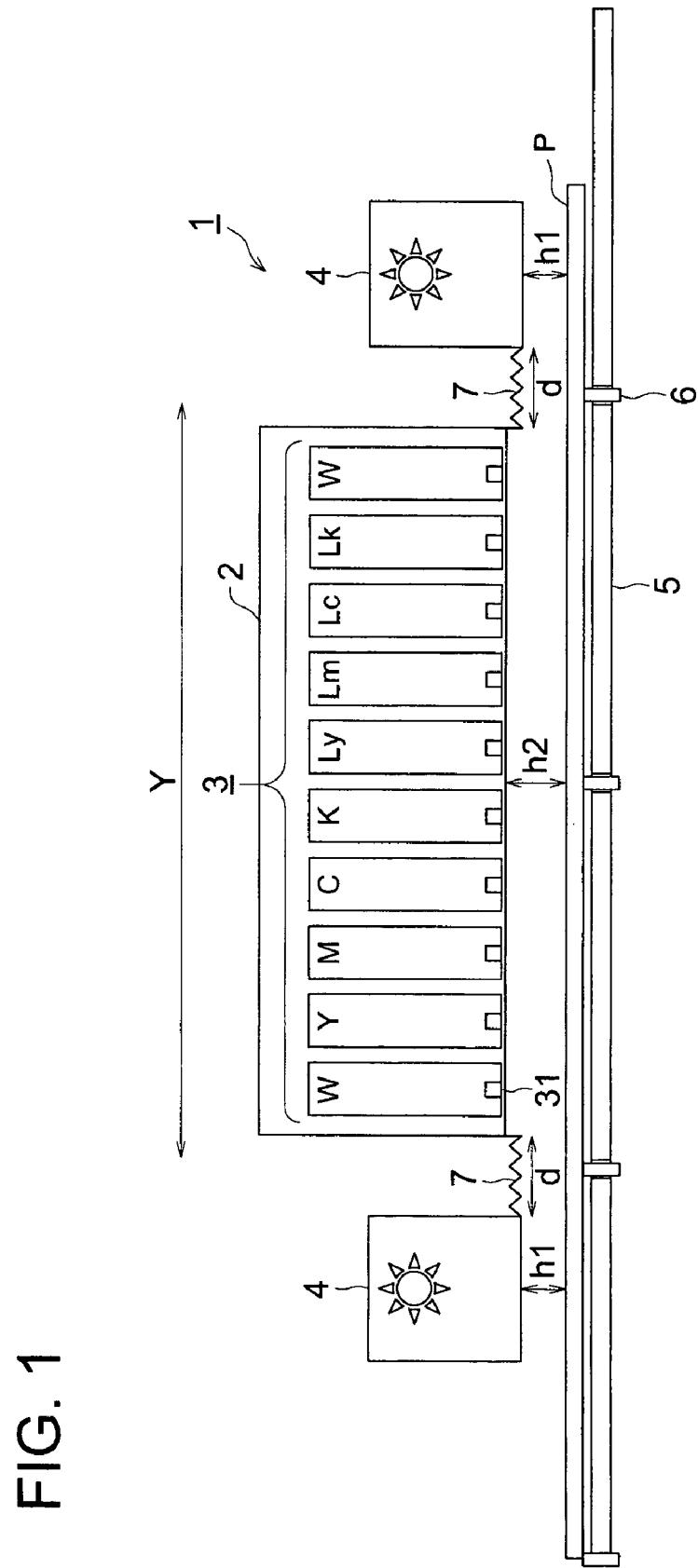
FIG. 1 is a front view illustrating a main constitution of a recording apparatus of the invention.

The above object has been achieved by the following constitutions.

1. An actinic ray curable composition containing a photo acid generator, and an oxetane compound I represented by the following formula 1,

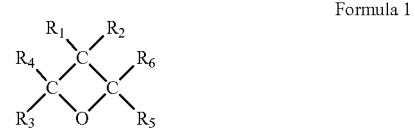

Formula 1 wherein $R_1$, $R_2$, $R_3$, $R_4$, $R_5$, and $R_6$ independently represent a hydrogen atom, a fluorine atom, an alkyl group having from 1 to 6 carbon atoms, a fluoroalkyl group having from 1 to 6 carbon atoms, an allyl group, an aryl group, a furyl group or a thienyl group, and wherein the longer C—O bond distance of the two C—O bond distances in formula 1 is from 0.1464 to 0.1500 nm.

2. The actinic ray curable composition of item 1 above, wherein $R_3$, $R_4$, $R_5$ and $R_6$ in formula 1 atom are not simultaneously hydrogen atoms.

3. The actinic ray curable composition of item 1 above, wherein the composition further contains an oxetane compound II having one oxetane ring which falls outside formula 1 or an oxetane compound III having two or more oxetane rings.

4. The actinic ray curable composition of item 1 above, wherein the composition further contains an oxirane compound having an oxirane ring.

5. The actinic ray curable composition of item 1 above, wherein the composition has a viscosity at 25° C. of from 7 to 50 mPa·s.

6. An actinic ray curable composition containing a photo acid generator, and an oxetane compound I' represented by the following formula 1,

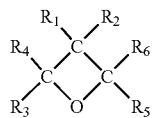

Formula 1 wherein $R_1$, $R_2$, $R_3$, $R_4$, $R_5$, and $R_6$ independently represent a hydrogen atom, a fluorine atom, an alkyl group having from 1 to 6 carbon atoms, a fluoroalkyl group having from 1 to 6 carbon atoms, an allyl group, an aryl group, a furyl group or a thienyl group, and wherein in formula 1, the longer C—O bond distance of the two C—O bond distances is from 0.1435 to 0.1461 nm, and the oxygen atom has a charge of from −0.330 to −0.281.

7. The actinic ray curable composition of item 6 above, wherein $R_3$, $R_4$, $R_5$ and $R_6$ in formula 1 atom are not simultaneously hydrogen atoms.

8. The actinic ray curable composition of item 6 above, wherein the composition further contains an oxetane compound II having one oxetane ring which falls outside formula 1 or an oxetane compound III having two or more oxetane rings.

9. The actinic ray curable composition of item 6 above, wherein the composition further contains an oxirane compound having an oxirane ring.

10. The actinic ray curable composition of item 6 above, wherein the composition has a viscosity at 25° C. of from 7 to 50 mPa·s.

11. An actinic ray curable ink, containing pigment, a photo acid generator, and an oxetane compound I represented by the following formula 1,

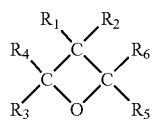

Formula 1 wherein $R_1$, $R_2$, $R_3$, $R_4$, $R_5$, and $R_6$ independently represent a hydrogen atom, a fluorine atom, an alkyl group having from 1 to 6 carbon atoms, a fluoroalkyl group having from 1 to 6 carbon atoms, an allyl group, an aryl group, a furyl group or a thienyl group, and wherein the longer C—O bond distance of the two C—O bond distances in formula 1 is from 0.1464 to 0.1500 nm.

12. An actinic ray curable ink, containing pigment, a photo acid generator, and an oxetane compound I' represented by the following formula 1,

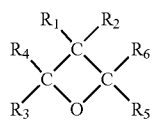

Formula 1 wherein $R_1$, $R_2$, $R_3$, $R_4$, $R_5$, and $R_6$ independently represent a hydrogen atom, a fluorine atom, an alkyl group having from 1 to 6 carbon atoms, a fluoroalkyl group having from 1 to 6 carbon atoms, an allyl group, an aryl group, a furyl group or a thienyl group, and wherein in formula 1, the longer C—O bond distance of the two C—O bond distances is from 0.1435 to 0.1461 nm, and the oxygen atom has a charge of from −0.330 to −0.281.

13. An image forming method comprising the steps of ejecting droplets of the actinic ray curable ink of item 11 above through a nozzle of an ink-jet recording head onto a recording material to deposit the ink on the recording material, and irradiating the ink on the recording material employing an actinic ray, 0.001 to 2.0 seconds after the ejected ink has been deposited on the recording material, whereby the cured ink layer is formed.

14. The image forming method of item 13 above, wherein the thickness of the cured ink layer is from 2 to 20 μm.

15. The image forming method of item 13 above, wherein the volume of the ink droplets to be ejected is from 2 to 15 pl.

16. The image forming method of item 13 above, wherein the ejecting of the actinic ray curable ink is carried out at 35 to 100° C.

17. An image forming method comprising the steps of ejecting droplets of the actinic ray curable ink of item 12 above through a nozzle of an ink-jet recording head onto a recording material to deposit the ink on the recording material, and irradiating the ink on the recording material employing an actinic ray, 0.001 to 2.0 seconds after the ejected ink has been deposited on the recording material, whereby the cured ink layer is formed.

18. The image forming method of item 17 above, wherein the thickness of the cured ink layer is from 2 to 20 μm.

19. The image forming method of item 17 above, wherein the volume of the ink droplets to be ejected is from 2 to 15 pl.

20. The image forming method of item 17 above, wherein the ejecting of the actinic ray curable ink is carried out at 35 to 100° C.

2-1. An actinic ray curable composition containing a photo acid generator, and an oxetane compound I represented by formula 1 above having an oxetane ring, wherein $R_1$, $R_2$, $R_3$, $R_4$, $R_5$, and $R_6$ independently represent a hydrogen atom, a fluorine atom, an alkyl group having from 1 to 6 carbon atoms, a fluoroalkyl group having from 1 to 6 carbon atoms, an allyl group, an aryl group, a furyl group or a thienyl group, and wherein the longer C—O bond distance of the two C—O bond distances in formula 1 is from 0.1464 to 0.1500 nm.

2-2. The actinic ray curable composition of item 2-1 above, wherein $R_3$, $R_4$, $R_5$ and $R_6$ in formula 1 atom are not simultaneously hydrogen atoms.

2-3. The actinic ray curable composition of item 2-1 or 2-2 above, wherein the composition contains a monofunctional oxetane compound having one oxetane ring and a bifunctional oxetane compound having two or more oxetane rings.

2-4. The actinic ray curable composition of any one of items 2-1 through 2-3 above, wherein the composition contains a compound having an oxirane ring.

2-5. The actinic ray curable composition of any one of items 2-1 through 2-4 above, wherein the composition has a viscosity at 25° C. of from 7 to 50 mPa·s.

2-6. An actinic ray curable ink comprising the composition of any one of items 2-1 through 2-5 above, and pigment.

2-7. An image forming method comprising the steps of ejecting the actinic ray curable ink of item 2-6 above through a nozzle of an ink-jet recording head onto a recording material to deposit the ink on the recording material, and irradiating the ink on the recording material employing an actinic ray, 0.001 to 2.0 seconds after the ejected ink has been deposited on the recording material, whereby the ink is cured to form an ink image.

2-8. An image forming method comprising the steps of ejecting the actinic ray curable ink of item 2-6 above through a nozzle of an ink-jet recording head onto a recording material to deposit the ink on the recording material, and irradiating the ink on the recording material employing an actinic ray to cure the ink to form a cured ink layer, the thickness of the cured ink layer being from 2 to 20μm.

2-9. An image forming method comprising the steps of ejecting droplets of the actinic ray curable ink of item 2-6 above through a nozzle of an ink-jet recording head onto a recording material to deposit the ink on the recording material, wherein the volume of the droplets of the ink to be ejected is from 2 to 15 pl.

2-10. An ink jet recording apparatus employing any one of the image forming methods of items 2-7 through 2-9, wherein the apparatus ejects the actinic ray curable ink at 35 to 100° C.

3-1. An actinic ray curable composition containing a photo acid generator, and an oxetane compound I' represented by formula 1 above having an oxetane ring, wherein $R_1$, $R_2$, $R_3$, $R_4$, $R_5$, and $R_6$ independently represent a hydrogen atom, a fluorine atom, an alkyl group having from 1 to 6 carbon atoms, a fluoroalkyl group having from 1 to 6 carbon atoms, an allyl group, an aryl group, a furyl group or a thienyl group, and wherein the longer C—O bond distance of the two C—O bond distances in formula 1 is from 0.1435 to 0.1461 nm, and the oxygen atom of formula 1 has a charge of from −0.330 to −0.281.

3-2. The actinic ray curable composition of item 3-1 above, wherein $R_3$, $R_4$, $R_5$ and $R_6$ in formula 1 atom are not simultaneously hydrogen atoms.

3-3. The actinic ray curable composition of item 3-1 or 3-2 above, wherein the composition contains a monofunctional oxetane compound having one oxetane ring and a bifunctional oxetane compound having two or more oxetane rings.

3-4. The actinic ray curable composition of any one of items 3-1 through 3-3 above, wherein the composition contains a compound having an oxirane ring.

3-5. The actinic ray curable composition of any one of items 3-1 through 3-4 above, wherein the composition has a viscosity at 25° C. of from 7 to 50 mPa·s.

3-6. An actinic ray curable ink comprising the composition of any one of items 3-1 through 3-5 above, and pigment.

3-7. An image forming method comprising the steps of ejecting droplets of the actinic ray curable ink of item 3-6 above through a nozzle of an ink-jet recording head onto a recording material to deposit the ink on the recording material, and irradiating the ink on the recording material employing an actinic ray, 0.001 to 2.0 seconds after the ejected ink has been deposited on the recording material, whereby the ink is cured to form an ink image.

3-8. An image forming method comprising the steps of ejecting droplets of the actinic ray curable ink of item 3-6 above through a nozzle of an ink-jet recording head onto a recording material to deposit the ink on the recording material, and irradiating the ink on the recording material employing an actinic ray to cure the ink to form a cured ink layer, the thickness of the cured ink layer being from 2 to 20 µm.

3-9. An image forming method comprising the steps of ejecting droplets of the actinic ray curable ink of item 3-6 above through a nozzle of an ink-jet recording head onto a recording material to deposit the ink on the recording material, wherein the volume of the droplets of the ink to be ejected is from 2 to 15 pl.

3-10. An ink jet recording apparatus employing any one of the image forming methods of items 3-7 through 3-9, wherein the apparatus ejects the actinic ray curable ink at 35 to 100° C.

It has been found that the use in the actinic ray curable composition of the oxetane compound I or I' represented by formula 1 containing an oxetane ring markedly improves curability of the composition and provides excellent curability regardless of curing conditions (temperature or humidity) under which the composition is cured. The oxetane compound represented by formula 1 is preferably an oxetane compound in which $R_3$, $R_4$, $R_5$, and $R_6$ in formula 1 are not simultaneously hydrogen atoms.

In Japanese Patent O.P.I. Publication No. 2001-181386 is disclosed a curable composition containing an oxetane compound. The oxetane compound disclosed therein is one in which the C—O bond distance defined in the invention falls outside the scope of the invention, and the curable composition provides insufficient curability, in which curability greatly varies due to curing conditions such as temperature or humidity condition, which cannot be put into practical use. In Japanese Patent O.P.I. Publication Nos. 2000-256571 and 2000-63371 are disclosed curable compositions containing an oxetane compound. However, these compositions are heat curable compositions, which objects are quite different from those of the invention.

The actinic ray curable ink of the invention, comprising the actinic ray curable composition of the invention and pigment, when it is employed as ink for an ink jet recording, is excellent in ink ejecting stability, which is the most important problem in ink jet recording. Further, the actinic ray curable ink of the invention makes it possible to easily control the dot diameter of the ink ejected onto recording material without being influenced by recording circumstances, and to form an image with good reproduction and high image quality. This ink is epoch-making.

Next, the present invention will be explained in detail.

First, the oxetane compound I or I' represented by formula 1 having an oxetane ring will be explained.

In formula 1, $R_1$, $R_2$, $R_3$, $R_4$, $R_5$, and $R_6$ independently represent a hydrogen atom or a substituent. It is preferred that $R_3$, $R_4$, $R_5$, and $R_6$ are not simultaneously hydrogen atoms.

In formula 1, examples of the substituent represented by $R_1$, $R_2$, $R_3$, $R_4$, $R_5$, and $R_6$ include a fluorine atom, an alkyl group having from 1 to 6 carbon atoms (for example, a methyl group, an ethyl group, a propyl group, a butyl group, etc.), a fluoroalkyl group having from 1 to 6 carbon atoms, an allyl group, an aryl group (for example, a phenyl group, a naphthyl group, etc.), a furyl group and a thienyl group. These groups described above are substituted or unsubstituted.

In the invention, the C—O bond distance in formula 1 is from 0.1464 to 0.1500 nm, wherein the bond distance in formula 1 (hereinafter also referred to as the C—O bond distance in the invention) represents the longer C—O bond distance of the two C—O bond distances in formula 1, or in formula 1, the C—O bond distance in the invention is from 0.1435 to 0.1461 nm and the charge of the oxygen atom is from −0.330 to −0.281.

The "charge" of the oxygen atom and "bond distance" herein referred to imply values obtained by molecular orbital calculation employing WinMOPAC (produced by FUJITU Co., Ltd.).

The content of the oxetane compound I or I' in the actinic ray curable composition is preferably from 5 to 90% by weight, and more preferably from 10 to 80% by weight, based on the total weight of the composition.

Examples of an oxetane compound II having one oxetane ring in the molecule, which falls outside formula 1, include oxetane compounds represented by the following formulae 2, 3, 4, and 5.

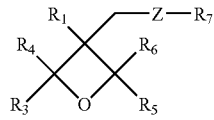

Formula 2

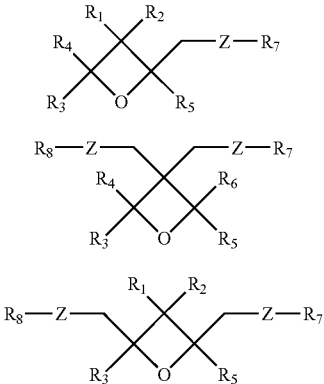

Formula 3

Formula 4

Formula 5

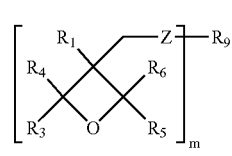

Formula 6

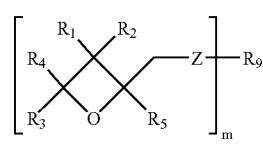

Formula 7

In formulae 2, 3, 4 and 5 above, $R_1$, $R_2$, $R_3$, $R_4$, $R_5$ and $R_6$ independently represent a hydrogen atom or a substituent, and Z represents an oxygen atom, a sulfur atom, a divalent hydrocarbon group or a divalent hydrocarbon group in which an oxygen atom or a sulfur atom is intervened.

In formulae 2, 3, 4 and 5 above, the substituent represented by $R_1$, $R_2$, $R_3$, $R_4$, $R_5$ and $R_6$ is the same as those denoted in $R_1$, $R_2$, $R_3$, $R_4$, $R_5$ and $R_6$ of formula 1.

In the formula 2 through 5, $R_7$ and $R_8$ independently represent an alkyl group having from 1 to 6 carbon atoms (for example, a methyl group, an ethyl group, a propyl group, a butyl group, etc.), an alkenyl group having from 2 to 6 carbon atoms (a 1-propenyl group, a 2-propenyl group, a 2-methyl-1-propenyl group, a 2-methyl-2-propenyl group, a 1-butenyl group, a 2-butenyl group, a 3-butenyl group, etc.), an aryl group (for example, a phenyl group, a naphthyl group, etc.), an aralkyl group (for example, a benzyl group, a fluorobenzyl group, a methoxybenzyl group), an acyl group having from 1 to 6 carbon atoms (a propylcarbonyl group, a butylcarbonyl group, a pentylcarbonyl group, etc.), an alkoxycarbonyl group having from 1 to 6 carbon carbons (for example, an ethoxycarbonyl group, a propoxycarbonyl group, a butoxycarbonyl group, etc.), an alkylcarbamoyl group having from 1 to 6 carbon atoms (for example, a propylcarbamoyl group, a butylpentylcarbamoyl group, etc.), and an alkoxycarbamoyl group (for example, an ethoxycarbamoyl group, etc.).

In formulae 2 through 5, the divalent hydrocarbon group represented by Z is an alkylene group (for example, an ethylene group, a trimethylene group, a tetramethylene group, a propylene group, an ethylethylene group, a pentamethylene group, a hexamethylene group, a heptamethylene group, an octamethylene group, a nonamethylene group, a decamethylene group, etc.), an alkenylene group (for example, a vinylene group, a propenylene group, etc.), an alkinylene group (an ethynylene group, or 3-pentynylene group, etc.). The divalent hydrocarbon group represented by Z in which an oxygen atom or a sulfur atom is intervened is the alkylene group, alkenylene group, or alkynyl group described above each having an oxygen atom or a sulfur atom intervened therein.

It is preferred in formulae 2 through 5 that $R_1$ is a lower alkyl group, and particularly an ethyl group, $R_7$ and $R_8$ are independently a propyl group, a phenyl group or a benzyl group, and Z is the divalent hydrocarbon group, particularly, an alkylene group, an alkenylene group, or an alkynylene group. It is also preferred in formulae 2 through 5 that $R_3$, $R_4$, $R_5$, and $R_6$ are not simultaneously hydrogen atoms.

Examples of an oxetane compound III having two or more oxetane rings in the molecule include compounds represented by the following formulae 6 and 7.

In formulae 6 and 7 above, m is 2, 3, or 4, and Z is the same as those denoted in Z of formulae 2 through 5.

$R_1$ through $R_6$ independently represent a hydrogen atom, a fluorine atom, an alkyl group having a carbon atom number of from 1 to 6 such as a methyl group, an ethyl group, a propyl group or a butyl group, a fluoroalkyl group having a carbon atom number of from 1 to 6, an allyl group, an aryl group, or a furyl group. In formula 6, it is preferred that $R_3$, $R_4$, $R_5$, and $R_6$ are not simultaneously hydrogen atoms.

$R_9$ represents a straight chain or branched chain alkylene group having from 1 to 12 carbon atoms, a straight chain or branched chain poly(alkylene oxy) group, or a divalent group selected from the group consisting of the following formula 9, 10 and 11. The straight chain or branched chain alkylene group having from 1 to 12 carbon atoms is preferably a group represented by the following formula 8.

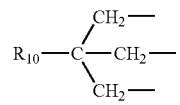

Formula 8

In formula 8, $R_{10}$ represents a lower alkyl group such as a methyl group, an ethyl group, or propyl group.

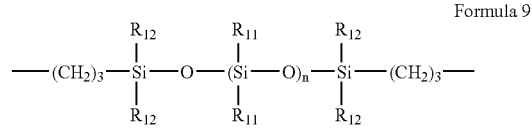

Formula 9

In the formula 9, "n" represents an integer of from 0 to 2000. $R_{11}$ represents an alkyl group having from 1 to 10 carbon atoms (for example, a methyl group, an ethyl group, a propyl group, a butyl group, a pentyl group, a hexyl group, a heptyl group, an octyl group, a nonyl group, etc.), or a group represented by the following formula 12. $R_{12}$ represents an alkyl group having from 1 to 10 carbon atoms (for example, a methyl group, an ethyl group, a propyl group, a butyl group, a pentyl group, a hexyl group, a heptyl group, an octyl group, a nonyl group, etc.).

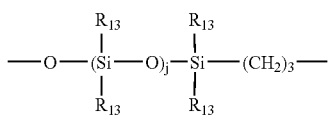

Formula 12

In the formula 12, "j" represents an integer of from 0 to 100. $R_{13}$ represents an alkyl group having from 1 to 10 carbon atoms (for example, a methyl group, an ethyl group, a propyl group, a butyl group, a pentyl group, a hexyl group, a heptyl group, an octyl group, a nonyl group, etc.).

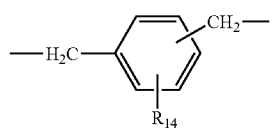

Formula 10

In the formula 10, $R_{14}$ represents an alkyl group having from 1 to 10 carbon atoms (for example, a methyl group, an ethyl group, a propyl group, a butyl group, a pentyl group, a hexyl group, a heptyl group, an octyl group, a nonyl group, etc.), an alkoxy group having from 1 to 10 carbon atoms (for example, a methoxy group, an ethoxy group, a propoxy group, a butoxy group, a pentoxy group, etc.), a halogen atom (for example, a fluorine atom, a chlorine atom, a bromine atom, a iodine atom, etc.), a nitro group, a cyano group, a mercapto group, an alkoxycarbonyl group (for example, a methyloxycarbonyl group, an ethyloxycarbonyl group, a butyloxycarbonyl group, etc.), or a carboxyl group.

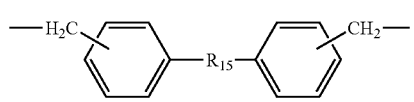

Formula 11

In the formula 10, $R_{15}$ represents an oxygen atom, a sulfur atom, —NH—, —SO—, —SO$_2$—, —(CH$_2$)—, —C(CH$_3$)$_2$— or —(CF$_3$)$_2$—.

A preferred partial structure in the molecule of the oxetane compound having an oxetane ring used in the invention will be explained below.

In formula 6 or 7, $R_1$ is preferably a lower alkyl group such as a methyl group, an ethyl group, or a propyl group, and more preferably an ethyl group. $R_9$ is preferably a hexamethylene group or one in which $R_{14}$ in formula 10 above is a hydrogen atom.

In formula 8 above, $R_{10}$ is preferably an ethyl group, and in formulae 9 and 12 above, $R_{12}$ and $R_{13}$ each are preferably hydrogen atoms. In formula 6 above, it is preferred that $R_3$ through $R_6$ are not simultaneously hydrogen atoms.

Examples of an oxetane compound III having two or more oxetane rings in the molecule include an oxetane compound represented by the following formulae 13.

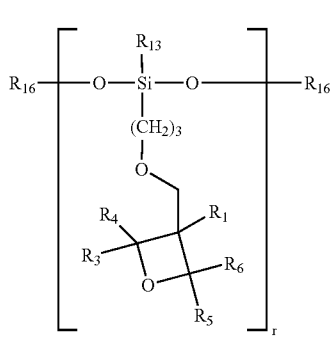

Formula 13

In the formula 13, r is an integer of from 25 to 200, $R_{16}$ represents an alkyl group having from 1 to 4 carbon atoms or a trialkylsilyl group. $R_1$ and $R_4$ through $R_6$ are the same as those denoted in formula 1. It is preferred that $R_3$ through $R_6$ are not simultaneously hydrogen atoms.

Exemplified compounds of the oxetane compound I represented by formula 1 wherein the longer C—O bond distance of the two C—O bond distances in formula 1 is form 0.1464 to 0.1500 nm, will be shown in Table 1 below, but the invention is not specifically limited thereto.

TABLE 1

Formula 1

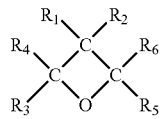

| Exemplified compound No. | $R_5$ | $R_6$ | RCR$_3$ | $R_4$ | $R_1$ | $R_2$ | *1 C—O bond distance (nm) |
|---|---|---|---|---|---|---|---|
| 1 | —CH$_3$ | H | H | H | —CH$_3$ | —CH$_3$ | 0.1464 |
| 2 | —CH$_2$CH$_3$ | H | H | H | —CH$_3$ | —CH$_3$ | 0.1464 |
| 3 | —CH$_2$CH$_2$CH$_3$ | H | H | H | —CH$_3$ | —CH$_3$ | 0.1464 |
| 4 | —CH(CH$_3$)CH$_3$ | H | H | H | —CH$_3$ | —CH$_3$ | 0.1464 |
| 5 | —(CH$_2$)$_7$CH$_3$ | H | H | H | —CH$_3$ | —CH$_3$ | 0.1464 |
| 6 | *2 | H | H | H | —CH$_3$ | —CH$_3$ | 0.1464 |
| 7 | —CH$_3$ | CH$_3$ | H | H | —CH$_3$ | —CH$_3$ | 0.1470 |
| 8 | —CH$_2$CH$_2$CH$_3$ | —CH$_2$CH$_2$CH$_3$ | H | H | —CH$_3$ | —CH$_3$ | 0.1475 |
| 9 | *2 | *2 | H | H | —CH$_3$ | —CH$_3$ | 0.1474 |
| 10 | *3 | H | —CFH$_2$ | H | —CH$_3$ | —CH$_3$ | 0.1464 |

TABLE 1-continued

Formula 1

R1, R2, R4, R3, R6, R5, O arranged around central C-C-C structure

| Exemplified compound No. | R5 | R6 | RCR3 | R4 | R1 | R2 | *1 C—O bond distance (nm) |
|---|---|---|---|---|---|---|---|
| 11 | *3 | H | —CF$_2$H | H | —CH$_3$ | —CH$_3$ | 0.1467 |
| 12 | —CH$_3$ | H | —CF$_2$H | H | —CH$_3$ | —CH$_3$ | 0.1468 |
| 13 | —CH$_3$ | H | —CF$_3$ | H | —CH$_3$ | —CH$_3$ | 0.1470 |
| 14 | *4 | H | H | H | —CH$_3$ | —CH$_3$ | 0.1472 |
| 15 | *5 | H | H | H | —CH$_3$ | —CH$_3$ | 0.1480 |
| 16 | *6 | H | H | H | —CH$_3$ | —CH$_3$ | 0.1463 |

*1: The C—O bond distance represents the longer C—O bond distance of the two C—O bond distances in formula 1.

Exemplified compound 7-2: a bifunctional compound corresponding to Exemplified compound 7

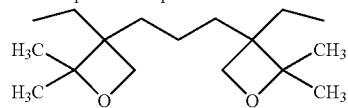

C—O bond distance: 0.1471 nm
Exemplified compound 7-3: a bifunctional compound corresponding to Exemplified compound 7 (with an ether bond)

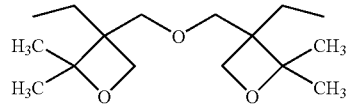

C—O bond distance: 0.1471 nm

*2
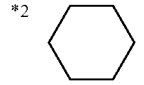

*3
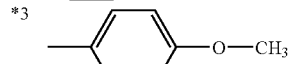

4

*5

CH$_3$
|
HC
|
CH$_3$

*6

H$_2$C
 \\
  HC=CH$_2$

Exemplified compounds 1-2 through 6-2 and 8-2 through 16-2 are cited as bifunctional compounds, which correspond to Exemplified compounds 1 through 6 and 8 through 16, respectively, in the same manner as in Exemplified compound 7-2, the bifunctional compound corresponding to Exemplified compound 7. Exemplified compounds 1-3 through 6-3 and 8-3 through 16-3 are cited as bifunctional compounds (having an ether bound), which correspond to Exemplified compounds 1 through 6 and 8 through 16 in the same manner as in Exemplified compound 7-3, the bifunctional compound (having an ether bond) corresponding to Exemplified compound 7.

Exemplified compounds of the oxetane compound I' in the invention represented by formula 1, in which in formula 1, the C—O bond distance in the invention is from 0.1435 to 0.1461 nm and the charge of the oxygen atom is form –0.330 to –0.281, will be shown in Table 2-1, but the invention is not specifically limited thereto.

TABLE 2-1

Formula 1

[Structure of Formula 1 with R1, R2, R3, R4, R5, R6 substituents on a four-membered ring containing O]

| Exemplified compound No. | R5 | R6 | R3 | R4 | R1 | R2 | *1 C—O bond distance (nm) | Charge of oxygen atom |
|---|---|---|---|---|---|---|---|---|
| 21 | CH₃ | H | CH₃ | H | —CH₃ | —CH₃ | 0.1461 | −0.281 |
| 22 | —CH₂CH₂CH₃ | H | CH₂CH₂CH₃ | H | —CH₃ | —CH₃ | 0.1461 | −0.283 |
| 23 | *7 | H | H | H | —CH₃ | —CH₃ | 0.1443 | −0.299 |
| 24 | —OCH₃ | H | H | H | —CH₃ | —CH₃ | 0.1445 | −0.301 |
| 25 | —OCH₂CH₃ | H | H | H | —CH₃ | —CH₃ | 0.1445 | −0.302 |

*1: The C—O bond distance represents the longer C—O bond distance of the two C—O bond distances in formula 1.
Exemplified compound 24-2: a bifunctional compound corresponding to Exemplified compound 24

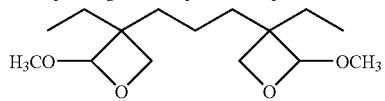

C—O bond distance: 0.1457 nm
Charge of oxygen atom: −0.299
Exemplified compound 24-3: a bifunctional compound corresponding to Exemplified compound 24 (with an ether bond)

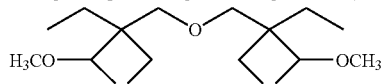

C—O bond distance: 0.1460 nm
Charge of oxygen atom: −0.296
*7

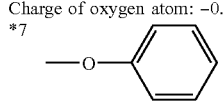

Exemplified compounds 21-2 through 23-2 and 25-2 are cited as bifunctional compounds, which correspond to Exemplified compounds 21 through 23 and 25, respectively, in the same manner as in Exemplified compound 24-2, a bifunctional compound corresponding to Exemplified compound 24. Exemplified compounds 21-3 through 23-3 and 25-3 are cited as bifunctional compounds (having an ether bond), which correspond to Exemplified compounds 21 through 23 and 25 in the same manner as in Exemplified compound 24-3, a bifunctional compound (having an ether bond) corresponding to Exemplified compound 24.

The above compounds can be synthesized according to the method described in Fourth item of "Kobunshikagaku to Yukikagaku tono Kyacchi Boru" or a method described in literatures described later. For example, they are synthesized mainly according to the following scheme, but the synthetic method is not specifically limited thereto.

Synthesis of Oxetane Compound I or I' of Formula 1

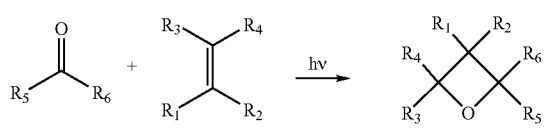

Synthesis of Oxetane Compound III of Formula 6

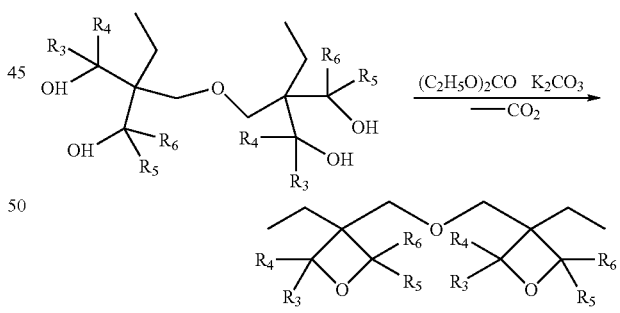

1. Hu Xianming, Richard M. Kellogg, Synthesis, 533–538, May (1955).
2. A. O. Fitton, J. Hill, D. Ejane, R. Miller, Synth., 12, 1140 (1987).
3. Toshiro Imai and Sinya Nishida, Can. J. Chem. Vol. 59, 2503–2509 (1981).
4. Nobujiro Shimizu, Shintaro Yamaoka, and Yuho Tsuno, Bull. Chem. Soc. Jpn., 56, 3853–3854 (1983).
5. Walter Fisher and Cyril A. Grob, Helv. Chim. Acta., 61, 2336 (1978).
6. Chem. Ber., 101, 1850 (1968).

7. "Heterocyclic Compounds with Three- and Four-membered Rings", Part Two, Chapter IX, Interscience Publishers, John Wiley & Sons, New York (1964).
8. H. A. J. Curless, "Synthetic Organic Photochemistry", Plenum, N.Y. (1984).
9. M. Broun, Nachr. Chem. Tech. Lab., 33, 213 (1985).
10. S. H. schroeter, J. Organic. Chem., 34, 5, 1151 (1969).
11. D. r. Arnold, Adv. Photochem., 6, 301 (1968).

Next, a photo acid generator generating an acid on exposure of light by will be explained. The photo acid generator herein referred to implies a compound generating an acid on light irradiation.

As the photo acid generator, for example, compounds used in a chemical amplification type photo resist or a light cationic polymerization composition are used (Organic electronics material seminar "Organic material for imaging" from Bunshin publishing house (1993), refer to page 187–192). Examples suitable for the present invention will be listed below.

Firstly, a $B(C_6F_5)_4^-$, $PF_6^-$, $AsF_6^-$, $SbF_6^-$, $CF_3SO_3^-$ salt of an aromatic onium compound such as an aromatic diazonium, ammonium, iodonium, sulfonium, or phosphonium compound, can be listed.

Examples of the onium compounds used in the invention will be shown below.

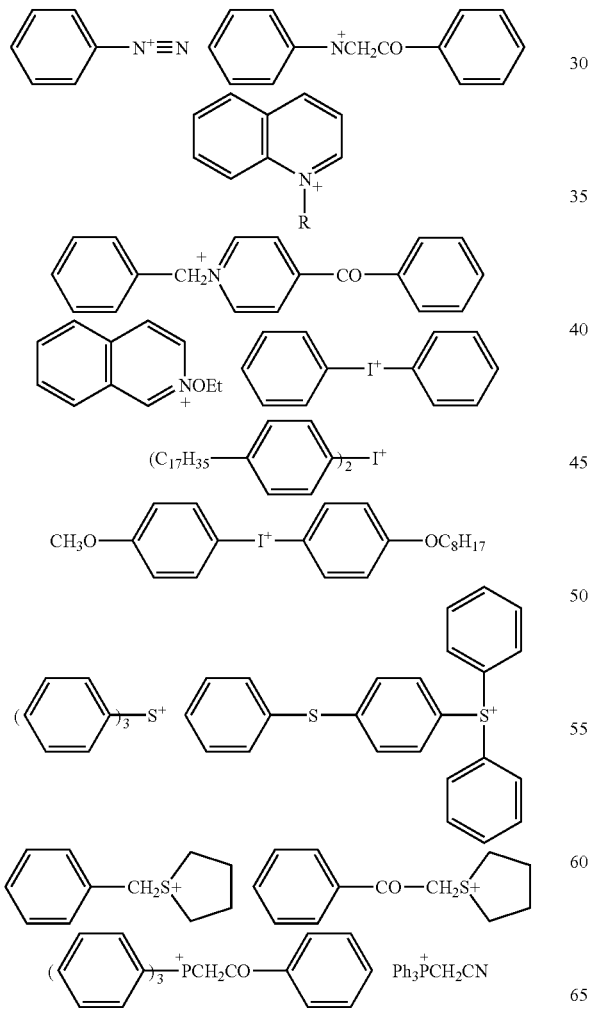

Secondly, sulfone compounds, which generate sulfonic acid, can be listed. Examples thereof will be shown below.

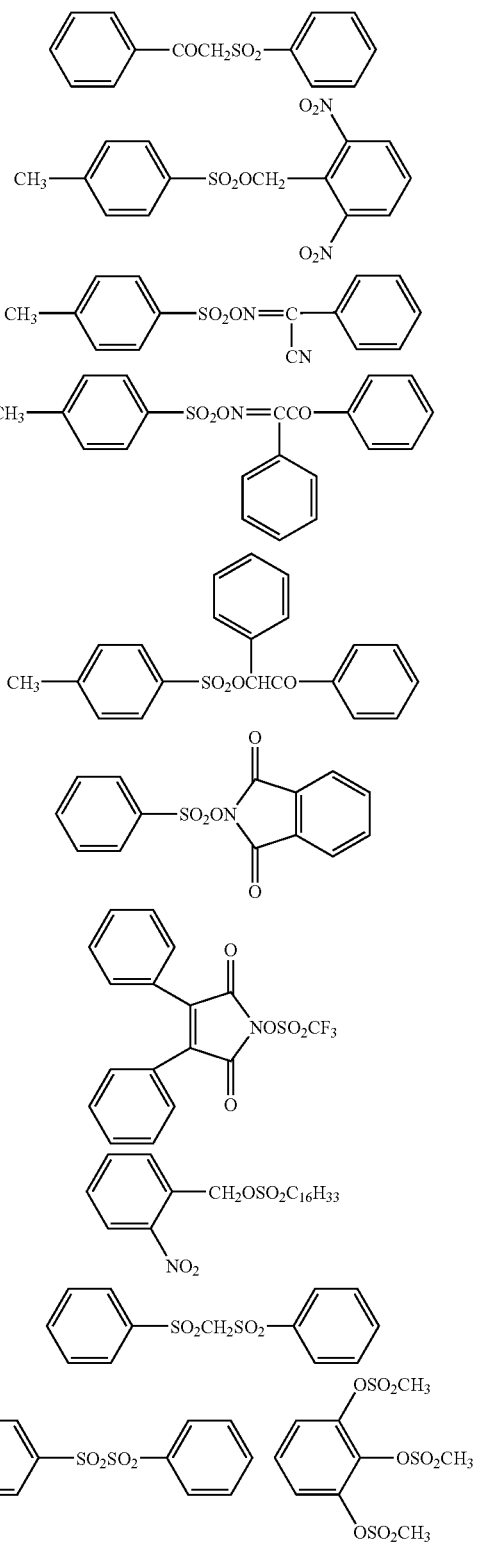

Thirdly, halide compounds, which generate hydrogen halide, can also be used. Example thereof will be shown below.

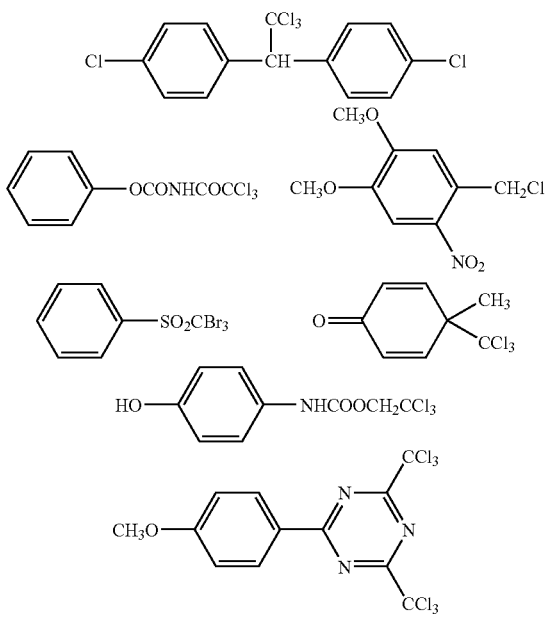

Fourthly, iron allene complexes can be listed.

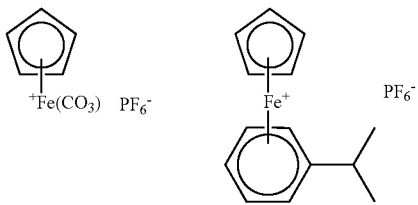

It is preferred that an acid increasing agent is added to the ink of the invention, which is well known and which newly generates an acid by the acid generated by actinic ray irradiation, as disclosed in, for example, JP-A Nos. H8-248561, and H9-034106. The addition of such an acid increasing agent can increase ink ejecting stability.

In the invention, known oxetane compounds other than the oxetane compound I or I' represented by formula (1) having an oxetane ring can be used in combination. Combined use of the oxetane compound I in the invention with an oxetane compound other than the oxetane compound in the invention having one oxetane ring or an oxetane compound having two or more oxetane rings is preferred in increasing strength of the cured ink or adhesion of ink to recording material.

In the invention, the actinic ray curable composition of the invention preferably contains a compound having an oxirane ring, in order to increase further curability.

The compound having an oxirane ring in the invention is a compound having in the molecule at least one oxirane ring represented by the following formula.

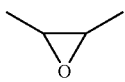

As such a compound, an epoxy resin is listed, which may be a monomer, an oligomer or a polymer.

The epoxy resins include an aromatic epoxide, an alicyclic epoxide, and an aliphatic epoxide, each being well known. Hereinafter, "epoxide" refers to an ethylene oxide monomer or an ethylene oxide oligomer. These compounds may be used singly or as an admixture of two or more thereof.

Epoxy compounds include an aromatic epoxide, an alicyclic epoxide and an aliphatic epoxide, which will be explained below.

A preferable aromatic epoxide is a di- or poly-glycidyl ether manufactured by a reaction of polyhydric phenol having at least one aromatic ring or of an alkylene oxide adduct thereof with epichlorohydrin, and includes, for example, such as di- or poly-glycidyl ether of bisphenol A or of an alkylene oxide adduct thereof, di- or poly-glycidyl ether of hydrogenated bisphenol A or of an alkylene oxide adduct thereof and novolac type epoxy resin. Herein, alkylene oxide includes such as ethylene oxide and propylene oxide.

An alicyclic epoxide is preferably a compound containing cyclohexene oxide or cyclopentene oxide obtained by epoxydizing a compound having at least one cycloalkane ring such as cyclohexene or cyclopentene by use of a suitable oxidizing agent such as hydrogen peroxide or a peracid.

A preferable aliphatic epoxide is such as di- or polyglycidyl ether of aliphatic polyhydric alcohol or of an alkylene oxide adduct thereof; the typical examples include diglycidyl ether of alkylene glycol, such as diglycidyl ether of ethylene glycol, diglycidyl ether of propylene glycol and diglycidyl ether of 1,6-hexane diol; polyglycidyl ether of polyhydric alcohol such as di- or triglycidyl ether of glycerin or of an alkylene oxide adduct thereof; and diglycidyl ether of polyalkylene glycol such as diglycidyl ether of polyethylene glycol or of an alkylene oxide adduct thereof and diglycidyl ether of polypropylene glycol or of an alkylene oxide adduct thereof. Herein, alkylene oxide includes such as ethylene oxide and propylene oxide.

Among these epoxides, aromatic epoxide and alicyclic epoxide are preferable and alicyclic epoxide is specifically preferable, taking a quick curing property in consideration. In the invention, one kind of epoxides described above alone may be utilized, and suitable combinations of two or more kinds thereof may also be utilized.

The actinic ray curable ink of the invention contains pigment in addition to the actinic ray curable composition as described above.

Pigments preferably utilized in the invention will be listed below:

C.I. Pigment Yellow-1, 3, 12, 13, 14, 17, 81, 83, 87, 95, 109, 42,

C.I. Pigment Orange-16, 36, 38,

C.I. Pigment Red-5, 22, 38, 48:1, 48:2, 48:4, 49:1, 53:1, 57:1, 63:1, 144, 146, 185, 101, C.I. Pigment Violet-19, 23, C.I. Pigment Blue-15:1, 15:3, 15:4, 4, 18, 60, 27, 29, C.I. Pigment Green-7, 36, C.I. Pigment White-6, 18, 21, C.I. Pigment Black-7, Further, in the invention, white ink is preferably utilized to increase a covering power of colors with transparent base materials such as a plastic film. It is preferable to utilize white ink, specifically in light package printing and label printing, however, due to increase of ejection amount, the using amount is naturally limited in respect to the abovementioned ejection stability, and generation of curl and wrinkles of a recording material.

To disperse the above-described pigment, for example, a ball mill, a sand mill, an attritor mill, a roll mill, an agitator, a Henshel mixer, a colloidal mixer, a ultrasonic homogenizer, a pearl mill, a wet jet mill, a paint shaker, etc. can be utilized. Further, a dispersant can be added at dispersion of a pigment. As a dispersant, a polymer dispersant is preferably utilized and Solsperse Series manufactured by Avecia Co. is included. Further, as a dispersion aid, a synergist corresponding to kinds of pigment can also be utilized. The dispersant and dispersion aid are preferably added in a range of from 1 to 50 weight parts based on 100 parts of pigment. As a dispersion medium, a solvent or a polymerizable compound is utilized, however, the actinic ray curable ink used in the invention is preferably an ink containing no solvent, since curing is carried out immediately after the ink has been deposited on recording material. When a solvent is left in the cured image, there cause problems of deterioration of resistance against solvents and VOC of residual solvent. Therefore, as a dispersion medium, polymerizable compounds are used but a solvent not. Particularly monomers having a lower viscosity among them are preferably used in view of dispersion suitability.

In dispersion of a pigment, selection of a pigment, a dispersant and a dispersion medium, dispersion conditions and filtering conditions are suitably set so as to make a mean particle diameter of a pigment of preferably from 0.08 to 0.5 µm and the maximum particle diameter of from 0.3 to 10 µm and preferably from 0.3 to 3 µm. By this particle diameter control, it is possible to depress clogging of a head nozzle and maintain stability of ink, as well as transparency and curing sensitivity of ink.

The pigment content of the actinic ray curable ink of the invention is preferably from 1 to 10% by weight based on the total ink.

The content of the oxetane compound I or I' in the actinic ray curable ink of the invention is preferably from 5 to 90% by weight, and more preferably from 10 to 80% by weight, based on the total weight of the ink.

Various kinds of additives other than those explained above can be added to the actinic ray curable ink of the invention. For example, a surfactant, a leveling additive, a matting agent, polyester type resin, polyurethane type resin, vinyl type resin, acryl type resin, rubber type resin and wax series can be added to the ink when necessary. Further, in order to increase storage stability, various basic compounds can be used. Examples of the basic compounds include a basic alkali metal compound, a basic alkali earth metal compound and an organic basic compound such as amine. The actinic ray curable ink of the invention may be a radical and cationic polymerization hybrid curable ink further containing a radical polymerization composition comprising a radical polymerization monomer and a radical initiator.

As a recording material used in the invention, besides ordinary non-coated paper or coated paper, various non-absorptive plastics or their films, which are used in a so-called light packaging, can be utilized. Examples of the plastic films include for example, a PET film, an OPS film, an OPP film, an ONy film, a PVC film, a PE film and a TAC film. As plastic films other than these, polycarbonate, acryl resin, ABS, polyacetal, PVA and a rubber series can be utilized. A metal series and a glass series are also applicable. The constitution of the invention becomes more effective especially when an image is formed particularly on a PET film, an OPS film, an OPP film, an ONy film and a PVC film, which are capable of thermally shrinking, of these recording materials. Generally, these recording materials are liable to cause curl and deformation of film due to such as curing shrinkage or heat generation at curing reaction of ink, and, in addition, a formed ink layer is hard to follow shrinkage of the materials.

Plastic films greatly differ in surface energy depending on the kinds, and heretofore, there has been a problem in that the ink dot diameter after ink deposition on recording material varies depending on the kinds of the recording materials. The constitution of the invention can form an image with high precision on recording materials having a surface energy of from 35 to 60 mN/m, the recording materials ranging from those having a low surface energy such as an OPP or OPS film to those having a relatively high surface energy such as a PET film.

In the invention, a long length roll (web) of a recording material is advantageously utilized in respect to a cost of a recording material such as a packaging cost and a manufacturing cost, an efficiency of print preparation and applicability to variety of print sizes.

An image forming method of the invention will be explained.

In the image forming method in the invention, it is preferred that the ink described above be ejected onto a recording material according to an ink jet recording method, and then cured by irradiation of actinic ray such as UV ray. (Thickness of ink layer formed after ink is ejected onto recording material)

In the invention, the thickness of an ink layer, after ink has been ejected onto recording material and cured by actinic ray irradiation, is preferably from 2 to 20 µm. In actinic ray curable ink jet recording in the field of screen printing, the total thickness of the ink is at present over 20 µm. Ink ejecting to give an excessive layer thickness is not preferred in the field of flexible package printing where a thin plastic film is used as a recording material, because problems are caused in that stiffness and texture of printed matter vary, in addition to problems of the aforementioned curl and wrinkles of recording material.

Herein, the thickness of ink layer refers to a maximum thickness of the ink layer deposited on recording material. This applies to a single color ink layer, and an overlapped layer of two different color (secondary color) inks, three different color inks or four different color inks (including white ink as a base ink), which are formed on recording material according to an ink jet recording process.

(Conditions of Ink Ejection)

As conditions of ink ejection, ink ejection is preferably performed while a recording head and ink are heated at from 35 to 100° C. in respect to ejection stability. Since actinic ray curable ink shows a large viscosity variation width depending on temperature variation and which in turn significantly influences a liquid droplet size and a liquid droplet ejection speed resulting in deterioration of image quality, it is required to keep an ink temperature constant while raising the ink temperature. A control width of ink temperature is a set temperature ±5° C., preferably a set temperature ±2° C. and furthermore preferably a set temperature ±1° C.

In the ink of the invention, the content of components in the actinic ray curable ink of the invention is preferably adjusted to give an ink viscosity at 25° C. of from 7 to 50 mPa.s in view of ink ejection stability.

In the invention, a droplet volume of the photo-curable ink ejected from nozzles of the ink jet recording head is preferably 2 to 15 pl.

The droplet volume of the ink has to be in the range described above to form images with high resolution, however, this droplet volume tends to lower the aforementioned ejection stability. In the invention, even when a small droplet volume such as 2 to 15 pl is ejected, ejection stability is improved, and images with high resolution can be formed.

(Actinic Ray Irradiation Condition after Ink has been Ejected onto Recording Material)

In an image recording method of the invention, it is preferred that actinic ray is irradiated 0.001 to 2.0 seconds after ink has been ejected on recording material, and it is more preferred that actinic ray is irradiated 0.001 to 1.0 second after ink has been ejected on recording material. It is specifically important that the irradiation timing be as early as possible in order to form an image with high resolution.

As an actinic ray irradiation method, a basic method is disclosed in JP-A No. 60-132767, in which light sources are provided at the both sides of a head unit where a head and a light are scanned in a shuttle mode. Irradiation is performed in a certain time interval after ink has been ejected onto recording material. Further, curing is completed by another light source which is not driven. As a light irradiation method, a method utilizing optical fiber, and a method in which collimated light source is reflected by a mirror provided on the side surface of a head unit and UV light (ultraviolet light) is irradiated on a recording portion are disclosed in U.S. Pat. No. 6,145,979. In an image forming method of the invention, any of these irradiation methods can be utilized.

Further, a method is also a preferable embodiment, in which actinic ray irradiation is divided into two steps; firstly, a first actinic ray irradiation is carried between the period from 0.001 to 2.0 seconds after ink was deposited on recording material by the above-described method and further a second actinic ray irradiation is carried after printing has been completed. Shrinkage of recording materials caused at the time of ink curing can be depressed by dividing actinic ray irradiation into two steps.

Heretofore, in a UV ink jet method, it has been usual to utilize a light source of high illuminance having a power exceeding 1 kW·hr in order to minimize widening of dots and bleeding-out caused after ink deposition on recording material. However, particularly in such as a shrink label, utilizing the light sources makes shrinkage of a recording material too large to be used practically at present.

In the invention, an actinic ray having a maximum illuminance in a wavelength range from 280 to 320 nm is preferably used, and even when a light source a power exceeding 1 kW·hr is used, images with high resolution can be formed, and shrinkage of a recording material is in the permissible range.

In the invention, the power of light sources irradiating an actinic ray is preferably less than 1 kW·hr. Examples of the light sources having a power of less than 1 kW·hr include a fluorescent lamp, a cold cathode tube and an LED, but are not limited thereto.

An ink jet recording apparatus (hereinafter also referred to as a recording apparatus) in the invention will be explained.

Next, the recording apparatus in the invention will be explained suitably in reference to a drawing. Herein, the recording apparatus of the drawing is only an embodiment of a recording apparatus of the invention, and a recording apparatus of the invention is not limited to the drawing.

FIG. 1 is a front view illustrating a main constitution of a recording apparatus of the invention. Recording apparatus 1 is equipped with head carriage 2, recording head 3, irradiation means 4 and platen portion 5. In recording apparatus 1, platen portion 5 is arranged under recording material P. Platen portion 5 has a UV ray absorbing function, and absorbs extra UV ray having passed through recording material P. As a result, images with high resolution can be reproduced quite stably.

Recording material P is guided by guide member 6 to be moved to the back side from the front side in FIG. 1 by operation of a transport means (not illustrated). Scan of recording head 3 held in head carriage 2 is made by reciprocating head carriage 2 in Y direction in FIG. 1 according to a head scanning means (not illustrated).

Head carriage 2 is provided over recording material P, and stores recording heads 3 described below with the ejection outlet 31 arranged downward, the number of recording heads 3 corresponding to the number of color inks used in an ink image printed on recording material. Head carriage 2 is provided in the main body of recording apparatus 1 so as to reciprocate in Y direction in FIG. 1 by a drive of a head scanning means.

Herein, FIG. 1 illustrates that head carriage 2 is supposed to store recording heads 3 of white (W), yellow (Y), magenta (M), cyan (C), black (K), light yellow (Ly), light magenta (Lm), light cyan (Lc), light black (Lk) and white (W), however, the number of recording heads 3 stored in head carriage 2 in practical operation is suitably determined.

Recording head 3 ejects an actinic ray curable ink (for example, UV curable ink) to be supplied by means of an ink supplying means (not illustrated) from its ejection outlets onto recording material P by action of plural ejecting means (not illustrated) equipped in the recording apparatus. A UV ink to be ejected by recording head 3 is comprised of a colorant, a polymerizing monomer, an initiator, etc., and is cured by cross-linking and polymerization initiated by UV irradiation of an initiator as a catalyst.

Recording head 3 ejects UV ink as an ink droplet onto a pre-determined region (a region capable of receiving the ink) of recording material P while the scan of the head is made in which the head moves from one edge to another of the recording material in a Y direction in FIG. 1 by drive of the head scanning means, whereby the UV ink is deposited on that region of the recording material.

The above scan is suitably made several times to eject UV ink onto one region of recording material. After that, while the recording material P is transported from the front side to the back side in FIG. 1 by transport means and the scan of the recording head 3 is again made by the head scan means, UV ink is ejected from the recording head onto the next region of the back side in FIG. 1 of recording material, which is adjacent to the one region on which the UV ink has been ejected.

The above operation is repeated, whereby the UV ink is ejected from recording head 3 employing the head scan means and the transport means to form an image comprised of aggregates of UV ink droplets on recording material P.

Irradiation means 4 is equipped with a UV lamp which emits ultraviolet ray with a specific wavelength region at a stable exposure energy and a filter which transmits ultraviolet ray with a specific wavelength. Herein, Examples of the UV lamp include a mercury lamp, a metal halide lamp, an eximer laser, a UV laser, a cold cathode tube, a black light, and an LED, and a metal halide lamp tube, a cold cathode tube, a mercury lamp tube and a black light, having a band-shape, are preferable. Specifically a cold cathode tube and a black light which emit a 365 nm ultraviolet ray are preferable, which can prevent bleeding-out, efficiently control a dot diameter, and reduce wrinkles on curing.

Utilizing a black light as a radiation source of irradiation means 4 reduces a manufacturing cost of irradiation means 4 for UV ink curing.

Irradiation means 4 has the possible largest size which can be installed in the recording apparatus 1 (an ink jet printer) or the irradiation region of the irradiation means 4 is larger than the largest region of recording material, onto which UV ink is ejected by one time scan of recording head 3 driven by a head scan means.

Irradiation means 4 is arranged by being fixed in nearly parallel with recording material 4 at the both sides of head carriage 2.

As described above, in order to adjust illuminance at an ink ejecting portion, it is natural to light-shield whole recording head 3, and, in addition, it is effective to make distance h2 between ink ejection outlet 31 of recording head 3 and recording material P longer than distance h1 between irradiation means 4 and recording material P (h1<h2) or to make distance d between recording head 3 and irradiation means 4 long (to make d large). Further, it is furthermore preferable to provide bellows structure 7 between recording head 3 and irradiation means 4.

Herein, wavelength of ultraviolet ray irradiated through irradiation means 4 can be suitably changed by changing a UV lamp or a filter, which is installed in irradiation means 4.

EXAMPLES

The invention will be explained according to the following examples, however, the invention is not specifically limited thereto.

Example 1

<<Preparation of Ink>>

Ink set 1 (Comparative) having the constitution as shown in Table 2 and Ink sets 2 through 5 (Inventive) having the constitution as shown in Tables 3 through 6 were prepared.

TABLE 2

| | | | | Ink Composition (% by weight) | | | | | |
|---|---|---|---|---|---|---|---|---|---|
| | | Colorant | | Photopolymerizable compound Oxetane compound | | Acid increasing | Thermal base generating agent | Photo acid | Sensitizing |
| | Kinds of ink | Kinds | Added amount | Comparative compound 1 | OXT-221 | agent Acpress 11M | Thermal base 1 | generator CI-5102 | dye CS-7001 |
| Ink set 1 (Comp.) | K | Colorant 1 | 5.0 | 41.0 | 45.0 | 1.0 | 0.01 | 5.0 | 3.0 |
| | C | Colorant 2 | 2.5 | 40.5 | 50.0 | 1.0 | 0.01 | 3.0 | 3.0 |
| | M | Colorant 3 | 3.0 | 40.0 | 50.0 | 1.0 | 0.01 | 3.0 | 3.0 |
| | Y | Colorant 4 | 2.5 | 40.5 | 50.0 | 1.0 | 0.01 | 3.0 | 3.0 |
| | W | Colorant 5 | 5.0 | 43.0 | 45.0 | 1.0 | 0.01 | 3.0 | 3.0 |
| | Lk | Colorant 1 | 0.6 | 42.4 | 50.0 | 1.0 | 0.01 | 3.0 | 3.0 |
| | Lc | Colorant 2 | 0.8 | 42.3 | 50.0 | 1.0 | 0.01 | 3.0 | 3.0 |
| | Lm | Colorant 3 | 0.6 | 42.4 | 50.0 | 1.0 | 0.01 | 3.0 | 3.0 |
| | Ly | Colorant 4 | 0.2 | 42.8 | 50.0 | 1.0 | 0.01 | 3.0 | 3.0 |

Comp.: Comparative

TABLE 3

| | | | | Ink Composition (% by weight) | | | | | |
|---|---|---|---|---|---|---|---|---|---|
| | | Colorant | | Photopolymerizable compound Oxetane compound | | Acid increasing | Thermal base generating agent | Photo acid | Sensitizing |
| | Kinds of ink | Kinds | Added amount | Exemplified compound 7 | OXT-221 | agent Acpress 11M | Thermal base 1 | generator CI-5102 | dye CS-7001 |
| Ink set 2 (Inv.) | K | Colorant 1 | 5.0 | 41.0 | 45.0 | 1.0 | 0.01 | 5.0 | 3.0 |
| | C | Colorant 2 | 2.5 | 40.5 | 50.0 | 1.0 | 0.01 | 3.0 | 3.0 |
| | M | Colorant 3 | 3.0 | 40.0 | 50.0 | 1.0 | 0.01 | 3.0 | 3.0 |
| | Y | Colorant 4 | 2.5 | 40.5 | 50.0 | 1.0 | 0.01 | 3.0 | 3.0 |

TABLE 3-continued

| | | Ink Composition (% by weight) | | | | | | |
|---|---|---|---|---|---|---|---|---|
| | | Colorant | | Photopolymerizable compound Oxetane compound | | Acid increasing agent | Thermal base generating agent | Photo acid generator | Sensitizing dye |
| Kinds of ink | Kinds | Added amount | Exemplified compound 7 | OXT-221 | Acpress 11M | Thermal base 1 | CI-5102 | CS-7001 |
| W | Colorant 5 | 5.0 | 43.0 | 45.0 | 1.0 | 0.01 | 3.0 | 3.0 |
| Lk | Colorant 1 | 1.3 | 41.7 | 50.0 | 1.0 | 0.01 | 3.0 | 3.0 |
| Lc | Colorant 2 | 0.6 | 42.4 | 50.0 | 1.0 | 0.01 | 3.0 | 3.0 |
| Lm | Colorant 3 | 0.8 | 42.2 | 50.0 | 1.0 | 0.01 | 3.0 | 3.0 |
| Ly | Colorant 4 | 0.6 | 42.4 | 50.0 | 1.0 | 0.01 | 3.0 | 3.0 |

Inv.: Inventive

TABLE 4

| | | | Ink Composition (% by weight) | | | | | | | |
|---|---|---|---|---|---|---|---|---|---|---|
| | | Colorant | | Photopolymerizable compound | | | Acid increasing agent | Basic compound *1 | Thermal base generating agent | Photo acid generator | Sensitizing dye |
| | | | | Epoxy | Oxetane compound | | | | | | |
| | Kinds of ink | Kinds | Added amount | compound DAIMIC | Exemplified compound 1 | OXT-212 | Acpress 11M | compound *1 | Thermal base 2 | Initiator 1 | CS-7102 |
| Ink set 3 (Inv.) | K | Colorant 1 | 5.0 | 15.0 | 46.1 | 24.8 | 3.0 | 0.01 | 0.1 | 5.0 | 1.0 |
| | C | Colorant 2 | 2.5 | 10.0 | 48.1 | 32.3 | 3.0 | 0.01 | 0.1 | 3.0 | 1.0 |
| | M | Colorant 3 | 3.0 | 10.0 | 48.1 | 31.8 | 3.0 | 0.01 | 0.1 | 3.0 | 1.0 |
| | Y | Colorant 4 | 2.5 | 10.0 | 48.1 | 32.3 | 3.0 | 0.01 | 0.1 | 3.0 | 1.0 |
| | W | Colorant 5 | 5.0 | 15.0 | 46.1 | 26.8 | 3.0 | 0.01 | 0.1 | 3.0 | 1.0 |
| | Lk | Colorant 1 | 1.3 | 10.0 | 47.5 | 34.2 | 3.0 | 0.01 | 0.1 | 3.0 | 1.0 |
| | Lc | Colorant 2 | 0.6 | 10.0 | 48.2 | 34.1 | 3.0 | 0.01 | 0.1 | 3.0 | 1.0 |
| | Lm | Colorant 3 | 0.8 | 10.0 | 48.0 | 34.2 | 3.0 | 0.01 | 0.1 | 3.0 | 1.0 |
| | Ly | Colorant 4 | 0.6 | 10.0 | 47.6 | 34.6 | 3.0 | 0.01 | 0.1 | 3.0 | 1.0 |

Inv.: Inventive

TABLE 5

| | | | Ink Composition (% by weight) | | | | | | | |
|---|---|---|---|---|---|---|---|---|---|---|
| | | Colorant | | Photopolymerizable compound | | | Acid increasing agent | Basic compound *2 | Thermal base generating agent | Photo acid generator | Sensitizing dye |
| | | | | Epoxy | Oxetane compound | | | | | | |
| | Kinds of ink | Kinds | Added amount | compound EPOLEAD | Exemplified compound 14 | OXT-221 | Compound 1 | compound *2 | Thermal base 1 | SP152 | DBA |
| Ink set 4 (Inv.) | K | Colorant 1 | 5.0 | 15.8 | 40.0 | 30.0 | 3.0 | 0.1 | 0.1 | 5.0 | 1.0 |
| | C | Colorant 2 | 2.5 | 21.8 | 40.0 | 30.0 | 1.5 | 0.1 | 0.1 | 3.0 | 1.0 |

TABLE 5-continued

Ink Composition (% by weight)

| | | | | Photopolymerizable compound | | | Acid increasing | | Thermal base generating | Photo | |
|---|---|---|---|---|---|---|---|---|---|---|---|
| | | | | | Oxetane compound | | agent | | agent | acid | Sensitizing |
| Kinds | Colorant | | Epoxy | Exemplified | | | | Basic | | | dye |
| of ink | Kinds | Added amount | compound EPOLEAD | compound 14 | OXT-221 | Compound 1 | compound *2 | Thermal base 1 | generator SP152 | DBA |
| M | Colorant 3 | 3.0 | 21.3 | 40.0 | 30.0 | 1.5 | 0.1 | 0.1 | 3.0 | 1.0 |
| Y | Colorant 4 | 2.5 | 21.8 | 40.0 | 30.0 | 1.5 | 0.1 | 0.1 | 3.0 | 1.0 |
| W | Colorant 5 | 5.0 | 19.3 | 40.0 | 30.0 | 1.5 | 0.1 | 0.1 | 3.0 | 1.0 |
| Lk | Colorant 1 | 1.3 | 23.1 | 40.0 | 30.0 | 1.5 | 0.1 | 0.1 | 3.0 | 1.0 |
| Lc | Colorant 2 | 0.6 | 23.7 | 40.0 | 30.0 | 1.5 | 0.1 | 0.1 | 3.0 | 1.0 |
| Lm | Colorant 3 | 0.8 | 23.6 | 40.0 | 30.0 | 1.5 | 0.1 | 0.1 | 3.0 | 1.0 |
| Ly | Colorant 4 | 0.6 | 23.7 | 40.0 | 30.0 | 1.5 | 0.1 | 0.1 | 3.0 | 1.0 |

Inv.: Inventive

TABLE 6

Ink Composition (% by weight)

| | | | | Photopolymerizable compound | | | Acid increasing | | Thermal base generating agent | | | |
|---|---|---|---|---|---|---|---|---|---|---|---|---|
| | | | | | Oxetane compound | | | | | | | |
| | Kinds of ink | Colorant Kinds | **2 | Epoxy compound Adecasizer | Exemplified compound 7-3 | Exemplified compound 7 | OXT-211 | agent Compound 2 | Basic compound *1 | Thermal base 2 | **3 **4 | **5 DBA |
| **1 | K | Colorant 1 | 5.0 | 8.4 | 20.0 | 35.0 | 25.0 | 3.0 | 0.01 | 0.1 | 2.5 | 1.0 |
| | C | Colorant 2 | 2.5 | 10.9 | 15.0 | 40.0 | 25.0 | 3.0 | 0.01 | 0.1 | 2.5 | 1.0 |
| | M | Colorant 3 | 3.0 | 10.4 | 15.0 | 40.0 | 25.0 | 3.0 | 0.01 | 0.1 | 2.5 | 1.0 |
| | Y | Colorant 4 | 2.5 | 10.9 | 15.0 | 40.0 | 25.0 | 3.0 | 0.01 | 0.1 | 2.5 | 1.0 |
| | W | Colorant 5 | 5.0 | 8.4 | 20.0 | 35.0 | 25.0 | 3.0 | 0.01 | 0.1 | 2.5 | 1.0 |
| | Lk | Colorant 1 | 1.3 | 12.1 | 15.0 | 40.0 | 25.0 | 3.0 | 0.01 | 0.1 | 2.5 | 1.0 |
| | Lc | Colorant 2 | 0.6 | 12.8 | 15.0 | 40.0 | 25.0 | 3.0 | 0.01 | 0.1 | 2.5 | 1.0 |
| | Lm | Colorant 3 | 0.8 | 12.6 | 15.0 | 40.0 | 25.0 | 3.0 | 0.01 | 0.1 | 2.5 | 1.0 |
| | Ly | Colorant 4 | 0.6 | 12.8 | 15.0 | 40.0 | 25.0 | 3.0 | 0.01 | 0.1 | 2.5 | 1.0 |

**1; Ink 5 (Inv.)
**2; Added amount
**3; Photo acid generator
**4; Initiator 2
**5; Sensitizing dye
Inv.: Inventive Details of each compound in the inks described in Tables 2 to 6 are as follows.
K: deep black ink
C: deep cyan ink
M: deep magenta ink
Y: deep yellow ink
Lk: light black ink
Lc: light cyan ink Lm: light magenta ink
Ly: light yellow ink
Colorant 1: C.I. pigment Black-7
Colorant 2: C.I. pigment Blue-15:3
Colorant 3: C.I. pigment Red-57:1
Colorant 4: C.I. pigment Yellow-13
Colorant 5: Titanium oxide (anatage type, average particle diameter: 0.20 μm)
Comparative compound 1: the C—O bond distance in the invention=0.1463 nm
OXT-211 (oxetane compound produced by Toa Gosei Kagaku Co., Ltd.): the C—O bond distance in the invention=0.1456 nm
OXT-212 (oxetane compound produced by Toa Gosei Kagaku Co., Ltd.): the C—O bond distance in the invention=0.1455 nm
OXT-221 (oxetane compound produced by Toa Gosei Kagaku Co., Ltd.): the C—O bond distance in the invention=0.1456 nm
DAIMIC: DAIMIC S300K epoxidated soy bean oil produced by Daicel Kagaku Co., Ltd.
EPOLEAD: EPOLEAD PB3600 epoxidated polybutadiene produced by Daicel Kagaku Co., Ltd.
Adecasizer: Adecasizer 0–130 epoxidated soy bean oil (admitted by FDA) produced by Asahi Denka Kogyo Co., Ltd.
Acpress 11: produced by Nippon Chemics Co., Ltd.
Acpress 11M: produced by Nippon Chemics Co., Ltd.
CGI552: produced by Ciba Specialty Chemicals Co., Ltd.
CS-7001: Naphthalene derivative, produced by Nippon Soda Co., Ltd.
CS-7102: Anthracene derivative, produced by Nippon Soda Co., Ltd.
SP152: produced by Asahi Denka Kogyo Co., Ltd.
DBA: produced by Kawasaki Kasei Kogyo Co., Ltd.
Basic compound *1: N-ethyldiethanolamine
Basic compound *2: Tributylamine

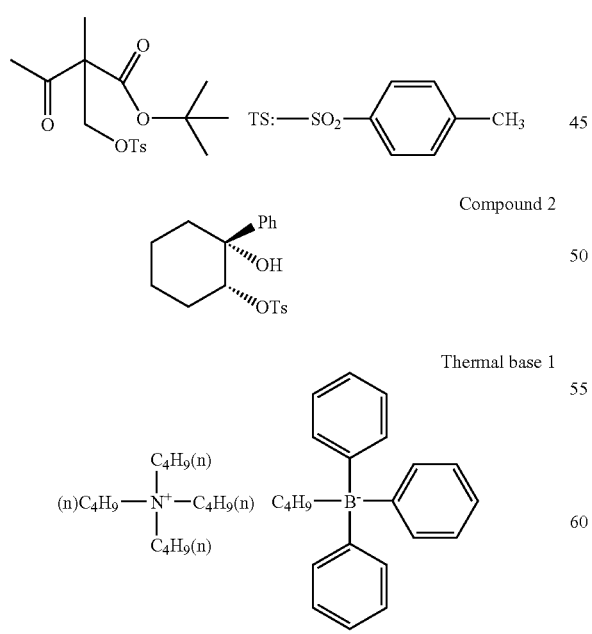

-continued

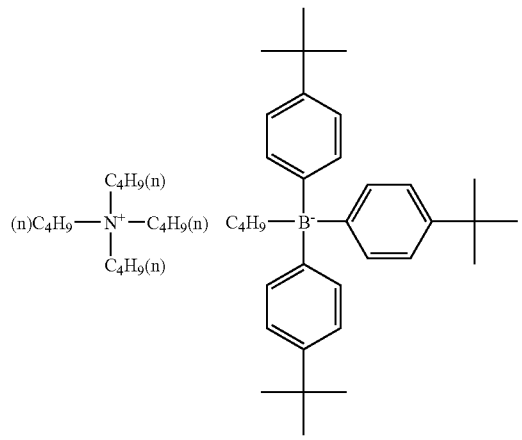

Thermal base 2

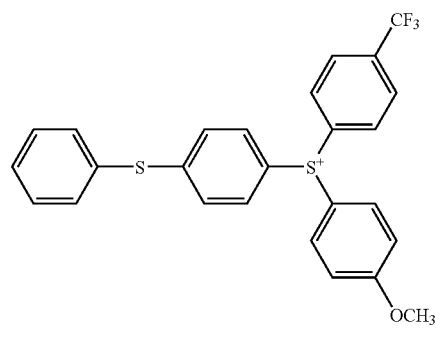

Initiator 1

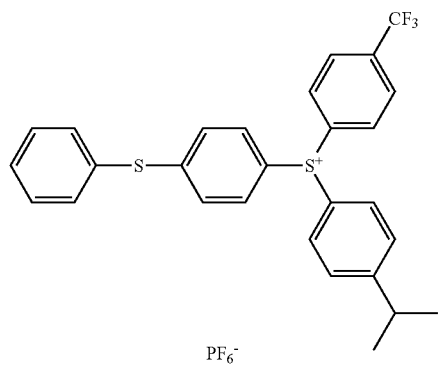

Initiator 2

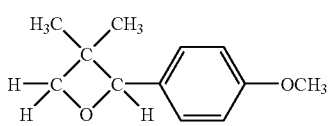

Comparative compound 1

Viscosity of each of the inks of the ink sets prepared above is as follows:

| | |
|---|---|
| Inks in Ink set 1: | 18 mPa · s |
| Inks in Ink set 2: | 18 mPa · s |
| Inks in Ink set 3: | 25 mPa · s |
| Inks in Ink set 4: | 30 mPa · s |
| Inks in Ink set 5: | 25 mPa · s |

<<Ink Jet Image Forming Method>>

An ink jet recording image was formed as follows.

Each ink set prepared as above was mounted on an ink jet recording apparatus as shown in FIG. 1 equipped with piezo-type ink jet nozzles, and image recording described later was performed continuously on each of 600 mm wide and 1000 m long recording materials having surface energy as shown in Table 7. An ink supply system is comprised of an ink tank, a supply pipe, a pre-chamber ink tank directly before a head, piping incorporating a filter, and a piezo-head, and the portion from a pre-chamber tank to a head was heat-insulated and heated at 50° C. The piezo-head being driven so as to eject ink with a droplet volume of from 2 to 15 pl at a resolution of 720 dpi×720 dpi to form a multi-sized dot image on recording material, the ink was continuously ejected. Curing was carried out after the ink was deposited on the recording material under the irradiation conditions as shown in Table 7. Curing was carried out 0.2 seconds after ink deposition with respect to samples 1 through 8, and 0.1 seconds after ink deposition with respect to samples 9 through 20. The thickness of the resulting ink layer was measured to be in a range of from 2.3 to 13 μm. Herein, dpi represents a dot number per 2.54 cm.

The above ink jet image recording were carried out under three recording circumstances, at 10° C. and 20% RH, at 25° C. and 50% RH, and at 32° C. and 80% RH, according to the image forming method described above.

In Table 7, abbreviation of each of the recording materials is as follows:
OPP: oriented polypropyrene
PET: polyethylene terephthalate
Shrink OPS: Oriented polystyrene for use of shrinkage available on the market Details of the light sources shown in Table 7 are as follows.
Light source 1: 120 W/cm metal halide lamp (MAL 400NL, produced by Nippon Denchi Co., Ltd., Output: 3 kW)
Light source 2: a cold cathode tube (produced by HYBECK Co., Ltd., Consumption power: less than 1 kW·hr)
Light source 3: LED (special order product produced by Nichia Kagaku Kogyo Co., Ltd., Consumption power: less than 1 kW·hr)

Details of the irradiation methods shown in Table 7 are as follows.
Irradiation method A: irradiation from both sides of a recording head employing a linear light source
Irradiation method B: irradiation from both sides of a recording head employing four 310 nm linear light sources and four 56 nm linear light sources
Irradiation method C: irradiation from both sides of a recording head employing twenty LED sources Thus, samples 1 through 20 as shown in Table 7 were obtained.

TABLE 7

| | | | | | | Irradiation condition | | | | |
|---|---|---|---|---|---|---|---|---|---|---|
| | | | | | | | on the recording material surface | | Light source used | |
| | | Recording materials | | Kinds | | *Peak | | Peak | | |
| Sample No. | Ink set No. | Kinds | Surface energy (mN/m) | of light source | Irradiation method | wave-length (nm) | Maximum illuminance (mW/cm²) | wave-length (nm) | Output power (mW/cm²) | Remarks |
| 1 | 1 | OPP | 38 | 1 | A | 365 | 650 | 365 | 180 | Comp. |
| 2 | 1 | PET | 53 | 1 | A | 365 | 650 | 365 | 180 | Comp. |
| 3 | 1 | **OPS | 39 | 1 | A | 365 | 650 | 365 | 180 | Comp. |
| 4 | 1 | ***paper | *1 | 1 | A | 365 | 650 | 365 | 180 | Comp. |
| 5 | 2 | OPP | 38 | 1 | A | 365 | 650 | 365 | 180 | Inv. |
| 6 | 2 | PET | 53 | 1 | A | 365 | 650 | 365 | 180 | Inv. |
| 7 | 2 | **OPS | 39 | 1 | A | 365 | 650 | 365 | 180 | Inv. |
| 8 | 2 | ***paper | *1 | 1 | A | 365 | 650 | 365 | 180 | Inv. |
| 9 | 3 | OPP | 38 | 2 | B | 365/310 | 15/10 | 365/310 | 50/33 | Inv. |
| 10 | 3 | PET | 53 | 2 | B | 365/310 | 15/10 | 365/310 | 50/33 | Inv. |
| 11 | 3 | **OPS | 39 | 2 | B | 365/310 | 15/10 | 365/310 | 50/33 | Inv. |
| 12 | 3 | ***paper | *1 | 2 | B | 365/310 | 15/10 | 365/310 | 50/33 | Inv. |
| 13 | 4 | OPP | 38 | 2 | B | 365/310 | 15/10 | 365/310 | 50/33 | Inv. |
| 14 | 4 | PET | 53 | 2 | B | 365/310 | 15/10 | 365/310 | 50/33 | Inv. |
| 15 | 4 | **OPS | 39 | 2 | B | 365/310 | 15/10 | 365/310 | 50/33 | Inv. |
| 16 | 4 | ***paper | *1 | 2 | B | 365/310 | 15/10 | 365/310 | 50/33 | Inv. |
| 17 | 5 | OPP | 38 | 3 | C | 380 | 40 | 380 | 80 | Inv. |
| 18 | 5 | PET | 53 | 3 | C | 380 | 40 | 380 | 80 | Inv. |
| 19 | 5 | **OPS | 39 | 3 | C | 380 | 40 | 380 | 80 | Inv. |
| 20 | 5 | ***paper | *1 | 3 | C | 380 | 40 | 380 | 80 | Inv. |

Inv.: Inventive,
Comp.: Comparative
*1; water absorptive
**OPS: Shrink OPS
***Paper: Cast-coated paper
*Peak wavelength refers to a wavelength giving maximum illuminance.

<Evaluation of Ink Jet Recording Images>

The resulting ink jet recording images under the three recording circumstances described above were evaluated according to the following evaluation methods.

(Character Quality)

6-point MS Minchyo (Ming-style) font characters were recorded at an intended density employing inks Y, M, C and K, and the resulting characters were evaluated for smoothness through a magnifying glass according to the following criteria. Herein, MS (Micro Soft™ Minchyo (Ming-style) font is one of the Japanese fonts for printing.

A: No roughness was observed.
B: Slight roughness was observed.
C: Roughness was observed, however, the resulting characters were legible, but at the lowest practical level.
D: Significant roughness was observed, and the resulting characters were scratchy, and were not acceptable for practical use.

(Color Contamination (or Bleeding-Out))

One dot of each of inks Y, M, C and K was recorded at 720 dpi to be adjacent to each other, and the resulting adjacent dots were evaluated for color contamination (or bleeding-out) through a magnifying glass according to the following criteria.

A: The shapes of adjacent dots where circular, with no bleeding-out observed.
B: The shapes of adjacent dots were nearly circular with little bleeding-out observed.
C: Adjacent dots showed some bleeding-out, and the dots were slightly deformed, but at the lowest practical level.
D: Adjacent dots showed bleeding-out and contaminated each other, which was not acceptable for practical use.

The results are shown in Table 8.

As is apparent from Table 8 above, the image recording method of the invention, which is carried out employing the inventive ink sets comprising the actinic ray curable composition of the invention, forms an image with high resolution with an excellent character quality, and exhibits no color contamination on various kinds of recording materials.

Example 2

Ink set 21 (Comparative) having the constitution as shown in Table 2-2 and Ink sets 22 through 25 (Inventive) having the constitution as shown in Tables 2-3 through 2-6 were prepared.

TABLE 8

| | Recording Circumstances | | | | | | |
|---|---|---|---|---|---|---|---|
| | 10° C., 20% RH | | 25° C., 50% RH | | 32° C., 80% RH | | |
| Sample No. | Character Quality | Color Contamination | Character Quality | Color Contamination | Character Quality | Color Contamination | Remarks |
| 1 | B | B | C | B | D | C | Comp. |
| 2 | B | B | B | C | D | D | Comp. |
| 3 | B | B | C | B | D | D | Comp. |
| 4 | B | B | B | C | C | D | Comp. |
| 5 | B | B | B | B | C | B | Inv. |
| 6 | B | B | B | B | B | C | Inv. |
| 7 | B | B | B | B | C | B | Inv. |
| 8 | A | A | A | B | B | B | Inv. |
| 9 | B | B | B | B | C | B | Inv. |
| 10 | B | A | B | A | B | A | Inv. |
| 11 | A | A | A | A | A | A | Inv. |
| 12 | A | A | A | A | A | A | Inv. |
| 13 | B | A | B | A | B | A | Inv. |
| 14 | A | A | A | A | A | B | Inv. |
| 15 | A | A | A | A | A | B | Inv. |
| 16 | A | B | A | B | A | B | Inv. |
| 17 | B | A | B | A | B | A | Inv. |
| 18 | A | A | A | A | A | B | Inv. |
| 19 | A | A | A | A | A | B | Inv. |
| 20 | A | A | A | A | A | A | Inv. |

Comp.: Comparative,
Inv.: Invention

TABLE 2-2

| | | | | Ink Composition (% by weight) | | | | |
|---|---|---|---|---|---|---|---|---|
| | | | | | Photopolymerizable compound Oxetane compound | | Acid increasing | Photo acid | Sensitizing |
| | Kinds of ink | Colorant Kinds | Added amount | Comparative compound 1 | OXT-221 | agent Acpress 11M | generator CGI552 | dye CS-7001 |
| Ink set 21 (Comp.) | K | Colorant 1 | 5.0 | 41.0 | 45.0 | 1.0 | 5.0 | 3.0 |
| | C | Colorant 2 | 2.5 | 40.5 | 50.0 | 1.0 | 3.0 | 3.0 |
| | M | Colorant 3 | 3.0 | 40.0 | 50.0 | 1.0 | 3.0 | 3.0 |
| | Y | Colorant 4 | 2.5 | 40.5 | 50.0 | 1.0 | 3.0 | 3.0 |
| | W | Colorant 5 | 5.0 | 43.0 | 45.0 | 1.0 | 3.0 | 3.0 |
| | Lk | Colorant 1 | 0.6 | 42.4 | 50.0 | 1.0 | 3.0 | 3.0 |
| | Lc | Colorant 2 | 0.8 | 42.3 | 50.0 | 1.0 | 3.0 | 3.0 |
| | Lm | Colorant 3 | 0.6 | 42.4 | 50.0 | 1.0 | 3.0 | 3.0 |
| | Ly | Colorant 4 | 0.2 | 42.8 | 50.0 | 1.0 | 3.0 | 3.0 |

Comp.: Comparative

TABLE 2-3

| | | | | Ink Composition (% by weight) | | | | |
|---|---|---|---|---|---|---|---|---|
| | | | | | Photopolymerizable compound Oxetane compound | | Acid increasing | Photo acid | Sensitizing |
| | Kinds of ink | Colorant Kinds | Added amount | Exemplified compound 23 | OXT-221 | agent Acpress 11M | generator CGI552 | dye CS-7001 |
| Ink set 22 (Inv.) | K | Colorant 1 | 5.0 | 41.0 | 45.0 | 1.0 | 5.0 | 3.0 |
| | C | Colorant 2 | 2.5 | 40.5 | 50.0 | 1.0 | 3.0 | 3.0 |
| | M | Colorant 3 | 3.0 | 40.0 | 50.0 | 1.0 | 3.0 | 3.0 |
| | Y | Colorant 4 | 2.5 | 40.5 | 50.0 | 1.0 | 3.0 | 3.0 |
| | W | Colorant 5 | 5.0 | 43.0 | 45.0 | 1.0 | 3.0 | 3.0 |
| | Lk | Colorant 1 | 1.3 | 41.8 | 50.0 | 1.0 | 3.0 | 3.0 |
| | Lc | Colorant 2 | 0.6 | 42.4 | 50.0 | 1.0 | 3.0 | 3.0 |
| | Lm | Colorant 3 | 0.8 | 42.3 | 50.0 | 1.0 | 3.0 | 3.0 |
| | Ly | Colorant 4 | 0.6 | 42.4 | 50.0 | 1.0 | 3.0 | 3.0 |

Inv.: Inventive

TABLE 2-4

| | | | | Ink Composition (% by weight) | | | | | |
|---|---|---|---|---|---|---|---|---|---|
| | | | | Photopolymerizable compound | | | | | |
| | | | | | Oxetane compound | | Acid increasing | Photo acid | |
| Kinds of ink | Colorant Kinds | Added amount | Epoxy compound DAIMIC | Exemplified compound 24 | OXT-212 | agent Acpress 11M | generator Initiator 1 | Sensitizing dye CS-7102 |
|---|---|---|---|---|---|---|---|---|
| Ink set 23 (Inv.) | K | Colorant 1 | 5.0 | 15.0 | 46.1 | 24.9 | 3.0 | 5.0 | 1.0 |
| | C | Colorant 2 | 2.5 | 10.0 | 48.1 | 32.4 | 3.0 | 3.0 | 1.0 |
| | M | Colorant 3 | 3.0 | 10.0 | 48.1 | 31.9 | 3.0 | 3.0 | 1.0 |
| | Y | Colorant 4 | 2.5 | 10.0 | 48.1 | 32.4 | 3.0 | 3.0 | 1.0 |
| | W | Colorant 5 | 5.0 | 15.0 | 46.1 | 26.9 | 3.0 | 3.0 | 1.0 |
| | Lk | Colorant 1 | 1.3 | 10.0 | 47.5 | 34.3 | 3.0 | 3.0 | 1.0 |
| | Lc | Colorant 2 | 0.6 | 10.0 | 48.2 | 34.2 | 3.0 | 3.0 | 1.0 |
| | Lm | Colorant 3 | 0.8 | 10.0 | 48.0 | 34.3 | 3.0 | 3.0 | 1.0 |
| | Ly | Colorant 4 | 0.6 | 10.0 | 47.6 | 34.8 | 3.0 | 3.0 | 1.0 |

Inv.: Inventive

TABLE 2-5

| | | | | Ink Composition (% by weight) | | | | | |
|---|---|---|---|---|---|---|---|---|---|
| | | | | Photopolymerizable compound | | | | | |
| | | | | | Oxetane compound | | Acid increasing | Photo acid | |
| Kinds of ink | Colorant Kinds | Added amount | Epoxy compound EPOLEAD | Exemplified compound 24-2 | OXT-212 | agent Compound 1 | generator SP152 | Sensitizing dye DBA |
|---|---|---|---|---|---|---|---|---|
| Ink set 24 (Inv.) | K | Colorant 1 | 5.0 | 16.0 | 40.0 | 30.0 | 3.0 | 5.0 | 1.0 |
| | C | Colorant 2 | 2.5 | 22.0 | 40.0 | 30.0 | 3.0 | 3.0 | 1.0 |
| | M | Colorant 3 | 3.0 | 21.0 | 40.0 | 30.0 | 3.0 | 3.0 | 1.0 |
| | Y | Colorant 4 | 2.5 | 22.0 | 40.0 | 30.0 | 3.0 | 3.0 | 1.0 |
| | W | Colorant 5 | 5.0 | 19.5 | 40.0 | 30.0 | 3.0 | 3.0 | 1.0 |
| | Lk | Colorant 1 | 1.3 | 23.3 | 40.0 | 30.0 | 3.0 | 3.0 | 1.0 |
| | Lc | Colorant 2 | 0.6 | 23.9 | 40.0 | 30.0 | 3.0 | 3.0 | 1.0 |
| | Lm | Colorant 3 | 0.8 | 23.8 | 40.0 | 30.0 | 3.0 | 3.0 | 1.0 |
| | Ly | Colorant 4 | 0.6 | 23.9 | 40.0 | 30.0 | 3.0 | 3.0 | 1.0 |

Inv.: Inventive

TABLE 2-6

| | | | Ink Composition (% by weight) | | | | | |
|---|---|---|---|---|---|---|---|---|
| | | | Photopolymerizable compound | | | Acid | Photo | |
| | | | | Oxetane compound | | increasing | acid | |
| Kinds | Colorant | | Epoxy | Exemplified | Exemplified | agent | generator | Sensitizing |
| of ink | Kinds | Added amount | compound Adecasizer | compound 24-3 | compound 24 | OXT-211 | Compound 2 | Initiator 2 | dye DBA |

| | Kinds of ink | Kinds | Added amount | Adecasizer | 24-3 | 24 | OXT-211 | Compound 2 | Initiator 2 | DBA |
|---|---|---|---|---|---|---|---|---|---|---|
| Ink set 25 (Inv.) | K | Colorant 1 | 5.0 | 8.4 | 20.0 | 35.0 | 25.0 | 3.0 | 2.5 | 1.0 |
| | C | Colorant 2 | 2.5 | 10.9 | 15.0 | 40.0 | 25.0 | 3.0 | 2.5 | 1.0 |
| | M | Colorant 3 | 3.0 | 10.4 | 15.0 | 40.0 | 25.0 | 3.0 | 2.5 | 1.0 |
| | Y | Colorant 4 | 2.5 | 10.9 | 15.0 | 40.0 | 25.0 | 3.0 | 2.5 | 1.0 |
| | W | Colorant 5 | 5.0 | 8.4 | 20.0 | 35.0 | 25.0 | 3.0 | 2.5 | 1.0 |
| | Lk | Colorant 1 | 1.3 | 12.1 | 15.0 | 40.0 | 25.0 | 3.0 | 2.5 | 1.0 |
| | Lc | Colorant 2 | 0.6 | 12.8 | 15.0 | 40.0 | 25.0 | 3.0 | 2.5 | 1.0 |
| | Lm | Colorant 3 | 0.8 | 12.6 | 15.0 | 40.0 | 25.0 | 3.0 | 2.5 | 1.0 |
| | Ly | Colorant 4 | 0.6 | 12.8 | 15.0 | 40.0 | 25.0 | 3.0 | 2.5 | 1.0 |

Inv.: Inventive

Details of the compounds used in the inks in Tables 2-2 to 2-6 are as follows.

Comparative compound 1: Charge of the oxygen atom=−0.279, the C—O bond distance in the invention=0.1463 nm OXT-211 (oxetane compound produced by Toa Gosei Kagaku Co., Ltd.): Charge of the oxygen atom=−0.275, the C—O bond distance in the invention=0.1456 nm OXT-212 (oxetane compound produced by Toa Gosei Kagaku Co., Ltd.): Charge of the oxygen atom=−0.280, the C—O bond distance in the invention=0.1455 nm OXT-221 (oxetane compound produced by Toa Gosei Kagaku Co., Ltd.): Charge of the oxygen atom=−0.275, the C—O bond distance in the invention=0.1456 nm CGI552: produced by Ciba Specialty Chemicals Co., Ltd.

Viscosity of each of the inks of the ink sets prepared above is as follows:

| Inks in Ink set 21: | 17 mPa · s |
| Inks in Ink set 22: | 17 mPa · s |
| Inks in Ink set 23: | 25 mPa · s |
| Inks in Ink set 24: | 28 mPa · s |
| Inks in Ink set 25: | 28 mPa · s |

<<Ink Jet Image Forming Method>>

An ink jet recording image was formed as follows.

Each ink set prepared as above was mounted on an ink jet recording apparatus as shown in FIG. 1 equipped with piezo-type ink jet nozzles, and image recording described later was performed continuously on each of 600 mm wide and 1000 m long recording materials having surface energy as shown in Table 2-7. An ink supply system is comprised of an ink tank, a supply pipe, a pre-chamber ink tank directly before a head, piping incorporating a filter, and a piezo-head, and the portion from a pre-chamber tank to a head was heat-insulated and heated at 50° C. The piezo-head being driven so as to eject ink with a droplet volume of from 2 to 15 pl at a resolution of 720 dpi×720 dpi to form a multi-sized dot image on recording material, the ink was continuously ejected. Curing was carried out after the ink was deposited on the recording material under the irradiation conditions as shown in Table 2-7. Curing was carried out 0.2 seconds after ink deposition with respect to samples 21 through 28, and 0.1 seconds after ink deposition with respect to samples 29 through 40. The thickness of the resulting ink layer was measured to be in a range of from 2.3 to 13 μm.

The above ink jet image recording were carried out under three recording circumstances, at 10° C. and 20% RH, at 25° C. and 50% RH, and at 32° C. and 80% RH, according to the image forming method described above.

Details of the light sources shown in Table 2-7 are as follows.

Light source 1: 120 W/cm metal halide lamp (MAL 400NL, produced by Nippon Denchi Co., Ltd., Output: 3 kW)

Light source 2: a cold cathode tube (produced by HYBECK Co., Ltd., Consumption power: less than 1 kW·hr)

Light source 3: LED (special order product produced by Nichia Kagaku Kogyo Co., Ltd., Consumption power: less than 1 kW·hr)

Details of the irradiation methods shown in Table 2-7 are as follows.

Irradiation method A: irradiation from both sides of a recording head employing a linear light source Irradiation method B: irradiation from both sides of a recording head employing four 310 nm linear light sources and four 365 nm linear light sources Irradiation method C: irradiation from both sides of a recording head employing twenty LED sources Thus, samples 2-1 through 2-20 as shown in Table 2-7 were obtained.

TABLE 2-7

| | | Recording materials | | Kinds of light source | Irradiation method | Irradiation condition on the recording material surface | | Light source used | | Remarks |
|---|---|---|---|---|---|---|---|---|---|---|
| Sample No. | Ink set No. | Kinds | Surface energy (mN/m) | | | *Peak wave-length (nm) | Maximum illuminance (mW/cm²) | *Peak wave-length (nm) | Output power (mW/cm²) | |
| 21 | 21 | OPP | 38 | 1 | A | 365 | 650 | 365 | 180 | Comp. |
| 22 | 21 | PET | 53 | 1 | A | 365 | 650 | 365 | 180 | Comp. |
| 23 | 21 | **OPS | 39 | 1 | A | 365 | 650 | 365 | 180 | Comp. |
| 24 | 21 | ***paper | *1 | 1 | A | 365 | 650 | 365 | 180 | Comp. |
| 25 | 22 | OPP | 38 | 1 | A | 365 | 650 | 365 | 180 | Inv. |
| 26 | 22 | PET | 53 | 1 | A | 365 | 650 | 365 | 180 | Inv. |
| 27 | 22 | **OPS | 39 | 1 | A | 365 | 650 | 365 | 180 | Inv. |
| 28 | 22 | ***paper | *1 | 1 | A | 365 | 650 | 365 | 180 | Inv. |
| 29 | 23 | OPP | 38 | 2 | B | 365/310 | 15/10 | 365/310 | 50/33 | Inv. |
| 30 | 23 | PET | 53 | 2 | B | 365/310 | 15/10 | 365/310 | 50/33 | Inv. |
| 31 | 23 | **OPS | 39 | 2 | B | 365/310 | 15/10 | 365/310 | 50/33 | Inv. |
| 32 | 23 | ***paper | *1 | 2 | B | 365/310 | 15/10 | 365/310 | 50/33 | Inv. |
| 33 | 24 | OPP | 38 | 2 | B | 365/310 | 15/10 | 365/310 | 50/33 | Inv. |
| 34 | 24 | PET | 53 | 2 | B | 365/310 | 15/10 | 365/310 | 50/33 | Inv. |
| 35 | 24 | **OPS | 39 | 2 | B | 365/310 | 15/10 | 365/310 | 50/33 | Inv. |
| 36 | 24 | ***paper | *1 | 2 | B | 365/310 | 15/10 | 365/310 | 50/33 | Inv. |
| 37 | 25 | OPP | 38 | 3 | C | 380 | 40 | 380 | 80 | Inv. |
| 38 | 25 | PET | 53 | 3 | C | 380 | 40 | 380 | 80 | Inv. |
| 39 | 25 | **OPS | 39 | 3 | C | 380 | 40 | 380 | 80 | Inv. |
| 40 | 25 | ***paper | *1 | 3 | C | 380 | 40 | 380 | 80 | Inv. |

Inv.: Inventive,
Comp.: Comparative
*1: Absorptive material
**OPS: Shrink OPS
***Paper: Cast-coated paper
*Peak wavelength refers to a wavelength giving maximum illuminance.

<Evaluation of Ink Jet Recording Images>

The resulting ink jet recording images under the three recording circumstances described above were evaluated in the same manner as in Example 1. the results are shown in Table 2-8.

TABLE 2-8

| | Recording Circumstances | | | | | | |
|---|---|---|---|---|---|---|---|
| | 10° C., 20% RH | | 25° C., 50% RH | | 32° C., 80% RH | | |
| Sample No. | Character Quality | Color Contamination | Character Quality | Color Contamination | Character Quality | Color Contamination | Remarks |
| 21 | B | B | C | B | D | C | Comp. |
| 22 | B | B | B | D | C | D | Comp. |
| 23 | B | B | B | B | D | D | Comp. |
| 24 | B | B | B | C | C | D | Comp. |
| 25 | B | B | B | B | C | B | Inv. |
| 26 | B | B | B | B | B | C | Inv. |
| 27 | B | B | B | B | B | B | Inv. |
| 28 | A | A | B | B | B | B | Inv. |
| 29 | B | A | B | A | C | A | Inv. |
| 30 | B | B | B | B | B | B | Inv. |
| 31 | A | A | A | A | A | A | Inv. |
| 32 | A | A | A | A | A | A | Inv. |
| 33 | B | A | B | A | B | A | Inv. |
| 34 | A | A | A | A | A | B | Inv. |
| 35 | B | A | B | A | B | B | Inv. |
| 36 | A | B | A | B | A | A | Inv. |
| 37 | B | A | B | A | B | A | Inv. |
| 38 | A | B | A | B | B | B | Inv. |
| 39 | A | A | A | A | A | B | Inv. |
| 40 | A | A | A | A | A | A | Inv. |

Comp.: Comparative,
Inv.: Invention

As is apparent from Table 2-8 above, the image recording method of the invention, which is carried out employing the inventive ink sets comprising the actinic ray curable composition of the invention, forms an image with high resolution with an excellent character quality, and exhibits no color contamination on various kinds of recording materials.

EFFECTS OF THE INVENTION

The invention can provide an actinic ray curable composition and an actinic ray curable ink, which provide an image with high resolution and excellent character quality, without causing color contamination under various recording circumstances, and an image recording method and an ink jet recording apparatus each employing the actinic ray curable ink.

What is claimed is:

1. An actinic ray curable composition containing a photo acid generator, and an oxetane compound I of the following formula,

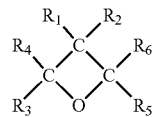

wherein $R_1$, $R_2$, $R_3$, $R_4$, $R_5$, and $R_6$ independently represent a hydrogen atom, a fluorine atom, an alkyl group having from 1 to 6 carbon atoms, a fluoroalkyl group having from 1 to 6 carbon atoms, an allyl group, an aryl group, a furyl group or a thienyl group, provided that $R_3$, $R_4$, $R_5$, and $R_6$, are not simultaneously hydrogen atoms, and wherein the longer C—O bond distance of the two C—O bond distances in formula is from 0.1464 to 0.1500 nm, and wherein the composition has a viscosity at 25° C. of from 7 to 50 mPa·s.

2. The actinic ray curable composition of claim 1, wherein the composition further contains an oxetane compound II represented by formula 2, 3, 4 or 5 or an oxetane compound III represented by formula 6 or 7,

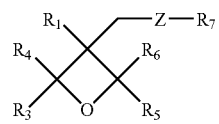
Formula 2

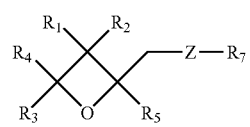
Formula 3

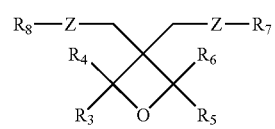
Formula 4

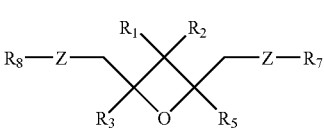
Formula 5 wherein $R_1$, $R_2$, $R_3$, $R_4$, $R_5$, and $R_6$ independently represent a hydrogen atom or a substituent, and Z represents an oxygen atom, a sulfur atom, a divalent hydrocarbon group or a divalent hydrocarbon group in which an oxygen atom or a sulfur atom is intervened,

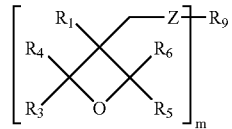
Formula 6

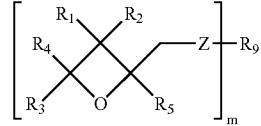
Formula 7 wherein $R_1$ through $R_6$ independently represent a hydrogen atom, a fluorine atom, an alkyl group having a carbon atom number of from 1 to 6 such as a methyl group, an ethyl group, a propyl group or a butyl group, a fluoroalkyl group having a carbon atom number of from 1 to 6, an allyl group, an aryl group, or a furyl group; m is 2, 3 or 4; Z represents an oxygen atom, a sulfur atom, a divalent hydrocarbon group or a divalent hydrocarbon group in which an oxygen atom or a sulfur atom is intervened; and $R_9$ represents a straight chain or branched chain alkylene group having from 1 to 12 carbon atoms, a straight chain or branched chain poly (alkylene oxy) group, or a divalent group selected from the group consisting of the following formula 9, 10 and 11,

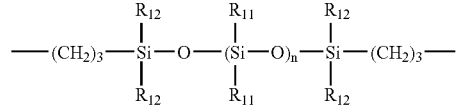
Formula 9 wherein n represents an integer of from 0 to 2000; $R_{11}$ represents an alkyl group having from 1 to 10 carbon atoms or a group represented by the following formula 12; and $R_{12}$ represents an alkyl group having from 1 to 10 carbon atoms,

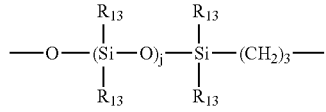
Formula 12 wherein j represents an integer of from 0 to 100; $R_{13}$ represents an alkyl group having from 1 to 10 carbon atoms,

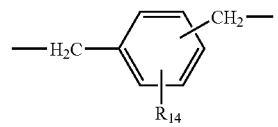
Formula 10 wherein $R_{14}$ represents an alkyl group having from 1 to 10 carbon atoms, an alkoxy group having from 1 to 10 carbon atoms, a halogen atom, a nitro group, a cyano group, a mercapto group, an alkoxycarbonyl group or a carboxyl group, Formula 11

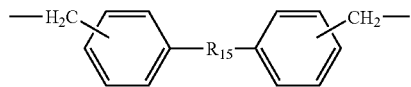

wherein $R_{15}$ represents an oxygen atom, a sulfur atom, —NH—, —SO—, —SO$_2$—, —(CH$_2$)—, —C(CH$_3$)$_2$— or —(CF$_3$)$_2$—.

3. The actinic ray curable composition of claim 1, wherein the composition further contains an oxirane compound having an oxirane ring.

4. An actinic ray curable composition containing a photo acid generator, and an oxetane compound I' of the following formula,

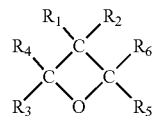

wherein $R_1$, $R_2$, $R_3$, $R_4$, $R_5$, and $R_6$, independently represent a hydrogen atom, a fluorine atom, an alkyl group having from 1 to 6 carbon atoms, a fluoroalkyl group having from 1 to 6 carbon atoms, an allyl group, an aryl group, a furyl group or a thienyl group, provided that $R_3$, $R_4$, $R_5$, and $R_6$, are not simultaneously hydrogen atoms, and wherein in the formula, the longer C—O bond distance of the two C—O bond distances is from 0.1435 to 0.1461 nm, and the oxygen atom has a charge of from −0.330 to −0.281, and wherein the composition has a viscosity at 25° C. of from 7 to 50 mPa·s.

5. The actinic ray curable composition of claim 4, wherein the composition further contains an oxetane compound II represented by formula 2, 3, 4 or 5 or an oxetane compound III represented by formula 6 or 7, Formula 2

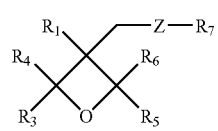

Formula 3

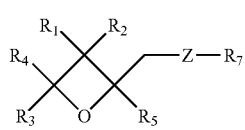

Formula 4

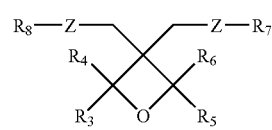

Formula 5

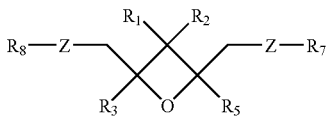

wherein $R_1$, $R_2$, $R_3$, $R_4$, $R_5$, and $R_6$, independently represent a hydrogen atom or a substituent, and Z represents an oxygen atom, a sulfur atom, a divalent hydrocarbon group or a divalent hydrocarbon group in which an oxygen atom or a sulfur atom is intervened, Formula 6

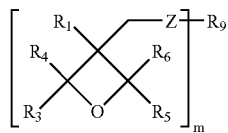

Formula 7

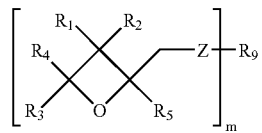

wherein $R_1$, through $R_6$, independently represent a hydrogen atom, a fluorine atom, an alkyl group having a carbon atom number of from 1 to 6 such as a methyl group, an ethyl group, a propyl group or a butyl group, a fluoroalkyl group having a carbon atom number of from 1 to 6, an allyl group, an aryl group, or a furyl group; m is 2, 3 or 4; Z represents an oxygen atom, a sulfur atom, a divalent hydrocarbon group or a divalent hydrocarbon group in which an oxygen atom or a sulfur atom is intervened; and $R_9$ represents a straight chain or branched chain alkylene group having from 1 to 12 carbon atoms, a straight chain or branched chain poly (alkylene oxy) group, or a divalent group selected from the group consisting of the following formula 9, 10 and 11, Formula 9

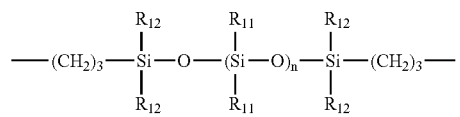

wherein n represents an integer of from 0 to 2000; $R_{11}$ represents an alkyl group having from 1 to 10 carbon atoms, or a group represented by the following formula 12; and $R_{12}$ represents an alkyl group having from 1 to 10 carbon atoms, Formula 12

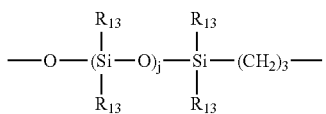

wherein j represents an integer of from 0 to 100; $R_{13}$ represents an alkyl group having from 1 to 10 carbon atoms,

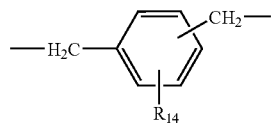
Formula 10 wherein $R_{14}$ represents an alkyl group having from 1 to 10 carbon atoms, an alkoxy group having from 1 to 10 carbon atoms, a halogen atom, a nitro group, a cyano group, a mercapto group, an alkoxycarbonyl group or a carboxyl group,

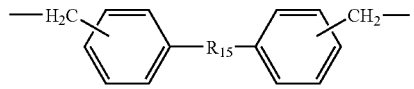
Formula 11 wherein $R_{15}$ represents an oxygen atom, a sulfur atom, —NH—, —SO—, —SO$_2$—, —(CH$_2$)—, —C(CR$_3$)$_2$— or —(CF$_3$)$_2$—.

6. The actinic ray curable composition of claim 4, wherein the composition further contains an oxirane compound having an oxirane ring.

7. An actinic ray curable ink, containing pigment, a photo acid generator, and an oxetane compound I of the following formula,

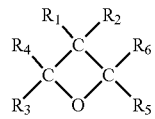

wherein $R_1$, $R_2$, $R_3$, $R_4$, $R_5$, and $R_6$, independently represent a hydrogen atom, a fluorine atom, an alkyl group having from 1 to 6 carbon atoms, a fluoroalkyl group having from 1 to 6 carbon atoms, an allyl group, an aryl group, a furyl group or a thienyl group, provided that $R_3$, $R_4$, $R_5$, and $R_6$, are not simultaneously hydrogen atoms, and wherein the longer C—O bond distance of the two C—O bond distances in the formula is from 0.1464 to 0.1500 nm, and wherein the composition has a viscosity at 25° C. of from 7 to 50 mPa·s.

8. An actinic ray curable ink, containing pigment, a photo acid generator, and an oxetane compound I' of the following formula,

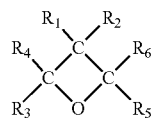

wherein $R_1$, $R_2$, $R_3$, $R_4$, $R_5$, and $R_6$, independently represent a hydrogen atom, a fluorine atom, an alkyl group having from 1 to 6 carbon atoms, a fluoroalkyl group having from 1 to 6 carbon atoms, an allyl group, an aryl group, a furyl group or a thienyl group, provided that $R_3$, $R_4$, $R_5$, and $R_6$, are not simultaneously hydrogen atoms, and wherein in the formula, the longer C—O bond distance of the two C—O bond distances is from 0.1435 to 0.1461 nm, and the oxygen atom has a charge of from −0.330 to −0.28l, and wherein the composition has a viscosity at 25° C. of from 7 to 50 mPa·s.

* * * * *